US010023612B2

(12) United States Patent
Eccleston et al.

(10) Patent No.: US 10,023,612 B2
(45) Date of Patent: Jul. 17, 2018

(54) METHOD OF TREATING ENDOMETRIOSIS

(71) Applicant: ValiRx PLC, London (GB)

(72) Inventors: Mark Eccleston, Wilburton (GB); Satu Vainikka, London (GB); George Steven Morris, London (GB)

(73) Assignee: VALIRX PLC, London (GB)

( * ) Notice: Subject to any disclaimer, the term of this patent is extended or adjusted under 35 U.S.C. 154(b) by 0 days.

(21) Appl. No.: 14/355,698

(22) PCT Filed: Nov. 1, 2012

(86) PCT No.: PCT/GB2012/052722

§ 371 (c)(1),
(2) Date: May 1, 2014

(87) PCT Pub. No.: WO2013/064830

PCT Pub. Date: May 10, 2013

(65) Prior Publication Data

US 2014/0322306 A1 Oct. 30, 2014

(30) Foreign Application Priority Data

Nov. 1, 2011 (GB) .................................. 1118831.5

(51) Int. Cl.

*A61K 38/00* (2006.01)
*C07K 7/06* (2006.01)
*C07K 5/097* (2006.01)
*C07K 7/08* (2006.01)
*G01N 33/68* (2006.01)
*C07K 5/117* (2006.01)
*C07K 16/18* (2006.01)
*C07K 16/28* (2006.01)
*A61K 47/64* (2017.01)

(52) U.S. Cl.

CPC .............. *C07K 7/06* (2013.01); *A61K 47/643* (2017.08); *A61K 47/646* (2017.08); *C07K 5/0821* (2013.01); *C07K 5/1024* (2013.01); *C07K 7/08* (2013.01); *C07K 16/18* (2013.01); *C07K 16/2869* (2013.01); *G01N 33/689* (2013.01); *A61K 38/00* (2013.01); *G01N 2333/723* (2013.01); *G01N 2500/02* (2013.01); *G01N 2800/364* (2013.01)

(58) Field of Classification Search

None

See application file for complete search history.

(56) References Cited

U.S. PATENT DOCUMENTS

| | | | |
|---|---|---|---|
| 5,288,707 | A | 2/1994 | Metternich |
| 5,550,251 | A | 8/1996 | Hirschmann et al. |
| 5,552,534 | A | 9/1996 | Hirschmann et al. |
| 7,863,289 | B2 | 1/2011 | Spevak et al. |
| 7,943,629 | B2 | 5/2011 | Luecking et al. |
| 7,956,053 | B2 | 6/2011 | Breitenstein et al. |
| 7,960,396 | B2 | 6/2011 | Honigberg et al. |
| 2008/0058358 | A1 | 3/2008 | Luecking et al. |
| 2008/0063654 | A1 | 3/2008 | McNeel et al. |
| 2008/0167338 | A1 | 7/2008 | Spevak et al. |
| 2009/0286821 | A1 | 11/2009 | Breitenstein et al. |
| 2010/0331350 | A1 | 12/2010 | Honigberg et al. |
| 2016/0065868 | A1 | 3/2016 | Vainikka et al. |

FOREIGN PATENT DOCUMENTS

| | | | |
|---|---|---|---|
| GB | 2496135 | A | 5/2013 |
| WO | WO 1998/046250 | A1 | 10/1998 |
| WO | WO 2000/001813 | A2 | 1/2000 |
| WO | WO 2008/113770 | * | 9/2008 |
| WO | WO 2008/113770 | A2 | 9/2008 |
| WO | WO 2009/132307 | A1 | 10/2009 |

(Continued)

OTHER PUBLICATIONS

Frackiewicz, Endometriosis: An Overview of the Disease and Its Treatment, J Am Pharm Assoc. 2000;40(5).*

Bladder cancer WebMD, download online on Jun. 15, 2015 from URL:<http://www.webmd.com/cancer/bladder-cancer/bladder-cancer-prevention>.*

Cervical cancer American cancer society, download online on Jun. 15, 2015 from URL:<http://www.cancer.org/cancer/cervicalcancer/moreinformation/cervicalcancerpreventionandearlydetection/cervical-cancer-prevention-and-early-detection-can-cervical-cancer-be-prevented>.*

Endometrial cancer American cancer society, download online on Jun. 15, 2015 from URL:<http://www.cancer.org/cancer/endometrialcancer/detailedguide/endometrial-uterine-cancer-prevention>.*

Endometriosis WebMD, download online on Jun. 15, 2015 from URL:<http://www.webmd.com/women/endometriosis/endometriosis-prevention>.*

(Continued)

*Primary Examiner* — Jennifer Pitrak McDonald

*Assistant Examiner* — Sergio Coffa

(74) *Attorney, Agent, or Firm* — Hamilton, Brook, Smith & Reynolds, P.C.

(57) ABSTRACT

The invention provides a molecule that inhibits or prevents an interaction between a Src family kinase and an androgen or estradiol receptor, for use in preventing or treating a non-cancerous condition in which an activity of AR and/or ER is a contributory factor in a subject, or for use in preventing or treating a cancerous condition in which an activity of AR and/or ER is a contributory factor in a subject who wishes to preserve fertility, or for use in preventing or treating a gynecological condition in which an activity of AR and/or ER is a contributory factor in a subject. Preferably, the molecule comprises or consists of the structure: $B_j$[(Pro)$_n$-$X_r$-His-Pro-His-Ala-Arg-Ile-Lys]$_m$-$R_p$, or $B_j$[lys-ile-arg-ala-his-pro-his-$x_r$-(pro)$_n$]$_m$-$R_p$, or a derivative or fragment thereof, wherein B is a first chemical moiety, j is 0 or 1, n is an integer from 1-10, X is any amino acid, r is an integer from 0 to 2, m is an integer from 1 to 3, R is a second chemical moiety, p is 0 or 1, and [lys-ile-arg-ala-his-pro-his-$x_r$-(pro)$_n$] is the retro-inverso peptide of [(Pro)$_n$-$X_r$-His-Pro-His-Ala-Arg-Ile-Lys].

1 Claim, 12 Drawing Sheets

(56) References Cited

FOREIGN PATENT DOCUMENTS

Figure 1:
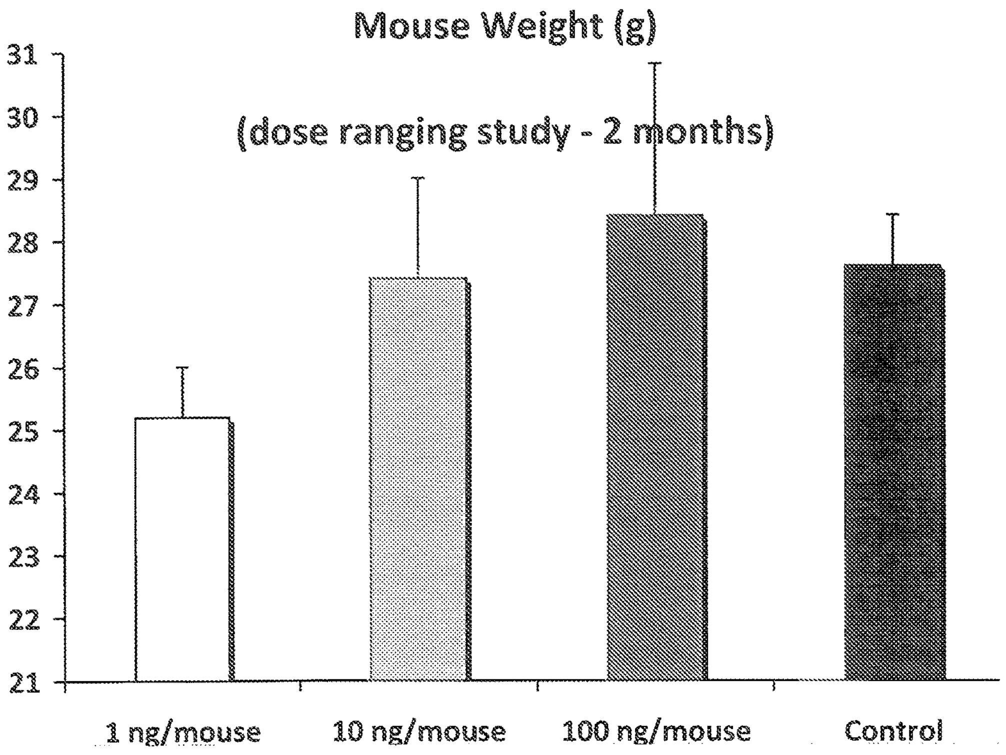

| | | | |
|---|---|---|---|
| WO | WO 2013/064830 | A2 | 5/2013 |
| WO | WO 2014/177868 | A2 | 11/2014 |

OTHER PUBLICATIONS

Healthline, download online on Jun. 15, 2015 from URL:<http://www.healthline.com/health/ovarian-cysts>.*

Ovarian cancer WebMD, download online on Jun. 15, 2015 from URL:<http://www.webmd.com/ovarian-cancer/guide/ovarian-cancer-prevention>.*

Prostate cancer American cancer society, download online on Jun. 15, 2015 from URL:<http://www.cancer.org/cancer/prostatecancer/detailedguide/prostate-cancer-prevention.*

Utah department of health, download online on Jun. 15, 2015 from URL:<http://www.ucan.cc/Cancer%20Education/Testicular_Cancer_FAQ/can-testicular-cancer-be-prevented.php>.*

Walker (Spermatogenesis 1:2, 116-120; Apr./May/Jun. 2011).*

Clement et al. (Nat. Rev. Urol. 8, 29-41 (2011)).*

Sonmezer et al. (The Oncologist May 2006 vol. 11 No. 5 422-434).*

Ailawardi, R.K., et al., "Treatment of endometriosis and chronic pelvic pain with letrozole and norethindrone acetate: a pilot study," *Fertility and Sterility*, 81(2): 290-296 (Feb. 2004).

Becker, C.M., et al., "Circulating Endothelial Progenitor Cells Are Up-Regulated in a Mouse Model of Endometriosis," *Am J Pathol*, 178(4): 1782-1791 (Apr. 2011).

Bodanszky, M., "VII. Techniques for the Facilitation of Peptide Synthesis", In *Principles of Peptide Synthesis*, Prof. Dr. Klaus Hafner, et al., eds. (NY: Springer-Verlag), pp. 233-251 (1984).

D'Cruz, O.J. and Uckun, F.M., "Targeting Mast Cells in Endometriosis with Janus Kinase 3 Inhibitor, JANEX-1," *Am J Reproductive Immunology*, 58(2): 75-97 (2007).

Deshayes, S. et al., "Interactions of Primary Amphipathic Cell Penetrating Peptides with Model Membranes: Consequences on the Mechanisms of Intracellular Delivery of Therapeutics," *Curr Pharm Des*, 11(28): 3629-3638 (2005).

Deshayes, S., et al., "Cell-penetrating peptides: tools for intracellular delivery of therapeutics," *Cell Mol Life Sci*, 62(16): 1839-1849 (2005).

Dugas, H. and Penney, C., In *Bioorganic Chemistry: A Chemical Approach to Enzyme Action*, Prof. C.R. Cantor, ed. (NY: Springer-Verlag), pp. 43-81 (1981).

Duncan, R.J.S., et al., "A New Reagent Which May Be Used to Introduce Sulfhydryl Groups into Proteins, and Its Use in the Preparation of Conjugates for Immunoassay," *Analyt Biochem*, 132: 68-73 (1983).

Giovannoni, L., et al., "Isolation of anti-angiogenesis antibodies from a large combinatorial repertoire by colony filter screening," *Nucleic Acids Res*, 29(5) e27:1-6 (2001).

Harlow, E., and Lane, D., In *Antibodies: A Laboratory Manual*, 1st Ed. (NY: Cold Spring Harbor Laboratory Press), ISBN 0-87969-314-2, 10 pgs. (1988).

Harlow, E., and Lane, D., In *Using Antibodies: A Laboratory Manual*, 2nd Ed. (NY: Cold Spring Harbor Laboratory Press) 3 pgs. (1999).

Janeway, Jr., C.A., et al., In *Immunobiology—5: The Immune System in Health and Disease*, (NY: Garland Publishing), ISBN 0-8153-3642-X, 12 pgs. (2001).

Kistner, R.W., "Conservative Management of Endometriosis", *Lancet*: 79(5): 179-183 (May 1959).

Kistner, R.W., "The Use of Newer Progestins in the Treatment of Endometriosis*," *Obstet. Gynecol.*, 75: 264-278 (1958).

Köhler, G. and Milstein C., "Continuous cultures of fused cells secreting antibody of predefined specificity," *Nature*, 256: 495-497 (Aug. 7, 1975).

Lindgren, M. et al., "Cell-penetrating peptides," *Trends Pharmacol. Sci.*, 21(3): 99-103 (Mar. 2000).

Longo, M. et al., "Interaction of estrogen receptor α with protein kinase C α and c-Src in osteoblasts during differentiation," *Bone*, 34: 100-111 (2004).

Lowe, C., et al., "Osteopetrosis in Src-deficient mice is due to an autonomous defect of osteoclasts," *Proc. Natl. Acad. Sci. USA*, 90: 4485-4489 (May 1993).

Luo, W., et al., "Global Impact of Oncogenic Src on a Phosphotyrosine Proteome," *Journal of Proteome Research*, 7(8): 3447-3460 (2008).

Matsuzaki, S., et al., "Effects of a protein kinase C inhibitor on the initial development of ectopic implants in a syngeneic mouse model of endometriosis," *Fertility and Sterility*, 89(1): 206-211, (Jan. 2008).

Merrifield, R.B., "Solid Phase Peptide Synthesis. I. The Synthesis of a Tetrapeptide,"*J Immunol*, 159(85): 2149-2154 (Jul. 20, 1963).

Mézière, C., et al., "In Vivo T Helper Cell Response to Retro-Inverso Peptidomimetics," *J Immunol*, 159: 3230-3237 (1997).

Migliaccio, A., et al., "Steroid Receptor Regulation of Epidermal Growth Factor Signaling through Src in Breast and Prostate Cancer Cells: Steroid Antagonist Action," Cancer Res, 65(22): 10585-10593 (Nov. 15, 2005).

Migliaccio, A., et al., "Steroid-induced androgen receptor-oestradiol receptor β-Src complex triggers prostate cancer cell proliferation," *The EMBO Journal*, 19(20): 5406-5417 (2000).

Moldenhauer, G., "Selection Strategies I: Monoclonal Antibodies," Chapter 2, *Handbook of Therapeutic Antibodies*, Published by Wiley-Vch, ed. Stefan Dubel, pp. 19-44 (2007).

Nairn, Ph.D., J.G., "Solutions, Emulsions, Suspension and Extractives", Chapter 84, In *Remington's Pharmaceutical Sciences 17th Edition*, A.R. Gennaro, ed. (PA: Mack Publishing Company), pp. 1492-1661 (1985).

Ngô, C., et al., "Protein kinase inhibitors can control the progression of endometriosis in vitro and in vivo," *J Pathol*, 222: 148-157 (2010).

O'Sullivan, M.J., et al., "Comparison of Two Methods of Preparing Enzyme-Antibody Conjugates: Application of These Conjugates for Enzyme Immunoassay," *Analyt Biochem*, 100: 100-108 (1979).

OuYang, Z., et al., "Interleukin-4 Stimulates Proliferation of Endometriotic Stromal Cells," *Am J Pathology*, 173(2): 463-469 (Aug. 2008).

Plant, A.L., et al., "Phospholipid/Alkanethiol Bilayers for Cell-Surface Receptor Studies by Surface Plasmon Resonance," *Analyt Biochem*, 226(2): 342-348 (1995).

Rich, D. H., "Inhibitors of cysteine Proteinases," Proteinase inhibitors, vol. 12, Chapter 4, In *Research Monographs in Cell and Tissue Physiology*, A.J. Barrett, et al., eds. (The Netherlands: Elsevier Science Publishers B.V.) pp. 153-178 (1986).

Sambrook, J. and Russell D.W., In *Molecular Cloning: A Laboratory Manual*, 3rd Edition, vols. 1-3 (NY: Cold Spring Harbor Laboratory Press), ISBN 0-87969-577-3, 23 pgs. (2001).

Schaffitzel, C., et al., "Ribosome display: an in vitro method for selection and evolution of antibodies from libraries," *J Immunol Methods*, 231: 119-135 (1999).

Schweppe, K.-W. and Hummelshoj, L., "Recommendations on the use of GnRH in the management of endometriosis," In *GnRH Analogs in Human Reproduction*, B. Luncnfcld, cd., (UK: Francis & Taylor), pp. 53-66 (2005).

Sherman, D.B. and Spatola, A.F., "Compatibility of Thioamides with Reverse Turn Features: Synthesis and Conformational Analysis of Two Model Cyclic Psuedopeptides Containing Thioamides as Backbone Modifications[1]," J. Am. Chem. Soc., 112(1): 433-441 (1990).

Takeuchi, T., et al., "Direct and Rapid Cytosolic Delivery Using Cell-Penetrating Peptides Mediated by Pyrenebutyrate," *ACS Chem Biol*, 1(5): 299-303 (2006).

Thompson, J.D. et al., "CLUSTAL W: improving the sensitivity of progressive multiple sequence alignment through sequence weighting, position-specific gap penalties and weight matrix choice," *Nucleic Acids Res*, 22(22): 4673-4680 (Nov. 11, 1994).

Thorsett, E.D., et al. "Dipeptide Mimics. Conformationally Restricted Inhibitors of Angiotensin-Converting Enzyme," *Biochem Biophys Res Commun*, 111(1): 166-171 (Feb. 28, 1983).

Veber, D. F., et al., "Conformationally restricted bicyclic analogs of somatostatin," *Proc. Natl. Acad. Sci. USA*, 75(6): 2636-2640 (Jun. 1978).

(56) References Cited

OTHER PUBLICATIONS

Venter, J.C., et al., "The Sequence of the Human Genome," *Science*, 291(5507): 1304-1351 (Feb. 16, 2001).
Vercellini, P., et al., "Continuous use of an oral contraceptive for endometriosis-associated recurrent dysmenorrhea that does not respond to a cyclic pill regimen," *Fertil Steril*, 80(3): 560-563 (Sep. 2003).
Walsh, L., ed., "A Novel Way to Model Endometriosis," *Research Horizons*, Issue 8:34, University of Cambridge (Spring 2009).
Wikipedia, "Endometriosis", [online], [retrieved on Oct. 8, 2011]. Retrieved from the Internet URL: http//en.wikipedia.org/wiki/Endometriosis.
Wikipedia,"Nuclear receptor coactivator 1", [online], [retrieved on Oct. 30, 2013]. Retrieved from the Internet URL: http//en.wikipedia.org/wiki/Nuclear_receptor_coactivator_1.
Winter, G., et al., "Making Antibodies by Phase Display Technology," *Annu. Rev. Immunol.*, 12: 433-455 (1994).
Yoshino, O., et al., "FR 167653, a p38 mitogen-activated protein kinase inhibitor, suppresses the development of endometriosis in a murine model," *J Repro Immunology*, 72: 85-93 (2006).
Zhou, W.-D., et al., "SB203580, a p38 mitogen-activated protein kinase inhibitor, suppresses the development of endometriosis by down-regulating proinflammatory cytokines and proteolytic factors in a mouse model," *Human Reproduction*, 25(12): 3110-3116 (2010).
Zola, H. and Brooks, D., "Techniques for the Production and Characterization of Monoclonal Hybridoma Antibodies," In *Monoclonal Hybridoma Antibodies: Techniques and Applications*, J.G.R. Hurrell, Ph.D., ed. (FL: CRC Press) pp. 1-57 (1982).
Zola, H., In *Monoclonal Antibodies: A Manual of Techniques*, (FL: CRC Press) pp. 3-11 and 147-181 (1987).
Kumagami, A., et al., "Expression patterns of the steroid receptor coactivator family in human ovarian endometriosis," *J. Obstet. Gynaecol. Res.*, 37(10): 1269-1276 (2011).
Migliaccio, A., et al., "Inhibition of the SH3 domain-mediated binding of Src to the androgen receptor and its effect on tumor growth," *Oncogene*, 26: 6619-6629 (2007).
Combined Search and Examination Report from British Application No. 1118831.5, "Medical Use," dated Feb. 28, 2012.
International Search Report and Written Opinion of the International Searching Authority from International Application No. PCT/GB2012/052722, "Medical Use," dated Jun. 28, 2013.
International Search Report and Written Opinion for Int'l Application No. PCT/GB2014/051347, titled: Modulators of the SRCE-Kinase Activity for Preventing or Treating Metastatic Cancer, dated Dec. 11, 2014.
International Preliminary Report on Patentability for Int'l Application No. PCT/GB2014/051347, titled: Modulators of the SRCE-Kinase Activity for Preventing or Treating Metastatic Cancer, Date of Issuance: Nov. 3, 2015.
Anonymous, "Pharmatest to exhibit and present new data at the AACR 2013 meeting," Retrieved from the internet: http://www.pharmatest.com/index.php/news/pharrnatest-exhibit-and-present-new-data -aacr-2013-meeting, Retrieved on: Jun. 7, 2016.
Auricchio, F. and A. Migliaccio, "VAL 201—An inhibitor of Androgen Receptor-associated Src and a Potential Treatment of Castration-resistant Prostate Cancer," *European Oncology and Haematology*, 8(1): 32-35 (Jan. 1, 2012).
Bogush, T. A., et al., "Estrogen Receptors, Antiestrogens, and Non-Small Cell Lung Cancer", *Biochemistry* (Moscow), vol. 75, No. 12: 1421-1427 (2010).
Castoria, G., et al., "Androgen-stimulated DNA synthesis and cytoskeletal changes in fibroblasts by a nontranscriptional receptor action", *The Journal of Cell Biology*, vol. 161, No. 3: 547-556 (2003).
Castoria, G., et al., "Androgen-Induced Cell Migration: Role of Androgen Receptor/Filamin A Association", *PLoSOne*, vol. 6, No. 2, e17218: 1-16 (2011).
Castoria, G., et al., "Tyrosine phosphorylation of estradiol receptor by Src regulates its hormone-dependent nuclear export and cell cycle progression in breast cancer cells", *Oncogene*, vol. 31: 4868-4877 (2012).
Chang, C., et al., "Structural analysis of complementary DNA and amino acid sequences of human and rat androgen receptors", *Proc. Natl. Acad. Sci.*, vol. 85: 7211-7215 (1988).
Chaudhuri, P. K., et al., "Presence of Steroid Receptors in Human Soft Tissue Sarcomas of Diverse Histological Origin", *Cancer Research*, vol. 40: 861-865 (1980).
Chauhan, S., et al., "Androgen Control of Cell Proliferation and Cytoskeletal Reorganization in Human Fibrosarcoma Cells: Role of RhoB Signaling", *J. Biol. Chem.*, vol. 279, No. 2: 937-944 (2004).
Cortes-Reynosa, P., et al., "Src kinase regulates metalloproteinase-9 secretion induced by type IV collagen in MCF-7 human breast cancer cells", *Matrix Biology*, vol. 27: 220-231 (2008).
Di Domenico, M., et al., "Estradiol Activation of Human Colon Carcinoma-derived Caco-2 Cell Growth", *Cancer Research*, vol. 56: 4516-4521 (1996).
Jung, H. H., et al., "Matrix Metalloproteinase-1 Expression Can Be Upregulated through Mitogen-Activated Protein Kinase Pathway under the Influence of Human Epidermal Growth Factor Receptor 2 Synergized with Estrogen Receptor", *Molecular Cancer Research*, vol. 8, No. 7: 1037-1047 (2010).
Knight, C. G., et al., "A novel coumarin-labelled peptide for sensitive continuous assays of the matrix metalloproteinases", *Federation of European Biochemical Societies*, vol. 296, No. 3: 263-266 (1992).
Lombardi, M., et al., "Hormone-dependent nuclear export of estradiol receptor and DNA synthesis in breast cancer cells", *J. Cell Biology*, vol. 182, No. 2: 327-340 (2008).
McCawley, L. J. and Matrisian, L. M., "Matrix metalloproteinases: they're not just for matrix anymore!", *Current Opinion in Cell Biology*, vol. 13: 534-540 (2001).
Migliaccio, A., et al., "Cross talk between epidermal growth factor (EGF) receptor and extra nuclear steroid receptors in cell lines", *Molecular and Cellular Endocrinology*, vol. 327: 19-24 (2010).
Migliaccio, A., et al., "Analysis of Androgen Receptor Rapid Actions in Cellular Signaling Pathways: Receptor/Src Association", *Androgen Action,Methods in Molecular Biology*, vol. 776: 361-370 (2011).
Morris, G.S. et al., "Abstract 2080: Inhibiting androgen receptor-associated Src signaling by VAL201 inhibits prostate cancer metastasis in an orthotopic mouse model," Retrieved from the internet: http://cancerres.aacrijournals.org/cgi/content/meeting_abstract/73/8_MectingAbstracts/2080, Retrieved on: Jul. 21, 2014.
Morris, G.S. et al., "Inhibiting androgen receptor-associated Src signaling by VAL201 inhibits prostate cancer metastasis in an orthotopic mouse model," Retrieved from the internet: http://www.pharmatest.com/files/4013/8022/1888/AACR_2013_poster_2080.pdf, Retrieved on: Jun. 7, 2016.
Murray, N. P. et al., "Differential Expression of Matrix Metalloproteinase-2 Expression in Disseminated Tumor Cells and Micrometastasis in Bone Marrow of Patients with Nonmetastatic and Metastatic Prostate Cancer: Theoretical Considerations and Clinical Implications—An Immunocytochemical Study", *Bone Marrow Research*, vol. 2012: 1-9 (2012).
Partridge, J. J., et al., "Functional Analysis of Matrix Metalloproteinases and Tissue Inhibitors of Metalloproteinases Differentially Expressed by Variants of Human HT-1080 Fibrosarcoma Exhibiting High and Low Levels of Intravasation and Metastasis", *The Journal of Biological Chemistry*, vol. 282, No. 49: 35964-35977 (2007).
Smith, M. M., et al., "Rapid Identification of Highly Active and Selective Substrates for Stromelysin and Matrilysin Using Bacteriophage Peptide Display Libraries", *The Journal of Biological Chemistry*, vol. 270, No. 12: 6440-6449 (1995).
Stabile, L. P., et al., "Human Non-Small Cell Lung Tumors and Cells Derived from Normal Lung Express Both Estrogen Receptor α and β and Show Biological Responses to Estrogen", *Cancer Research*, vol. 62: 2141-2150 (2002).
Suominen, M.I. et al., "Abstract 992: Inhibiting androgen receptor associated Src signaling with VAL201 inhibits breast cancer growth

(56) References Cited

OTHER PUBLICATIONS in an orthotopic xenograft model," Retrieved from the internet: http://cancerres.aacrjournals.org/cgi/content/meeting_abstract/73/8_MeetingAbstracts/922, Jun. 7, 2016.

Tuomela, J. M., et al., "Alendronate decreases orthotopic PC-3 prostate tumor growth and metastasis to prostate-draining lymph nodes in nude mice", *BMC Cancer*, vol. 8, No. 81: 12 pages (2008).

Tuomela, J., et al., "Overexpression of vascular endothelial growth factor C increases growth and alters the metastatic pattern of orthotopic PC-3 prostate tumors", *BMC Cancer*, vol. 9, No. 362: 12 pages (2009).

Valta, M. P., et al., "FGF-8b Induces Growth and Rich Vascularization in an Orthotopic PC-3 Model of Prostate Cancer", *Journal of Cellular Biochemistry*, vol. 107: 769-784 (2009).

Vanderschueren, D., et al., "Androgens and bone", *Current Opinion in Endocrinology, Diabetes & Obesity*, vol. 15: 250-254 (2008).

Varricchio, L., et al., "Inhibition of Estradiol Receptor/Src Association and Cell Growth by an Estradiol Receptor α Tyrosine-Phosphorylated Peptide", *Molecular Cancer Research*, vol. 5, No. 11: 1213-1221 (2007).

Verrijdt, G., et al., "Change of Specificity Mutations in Androgen-selective Enhancers", *The Journal of Biological Chemistry*, vol. 275, No. 16: 12298-12305 (2000).

* cited by examiner

FIGURE 3 (part 1 of 10)

Sequence Homology data - Androgen Receptor, Dihydro-testosterone receptor, Nuclear receptor family 3 group C member 4

[Sus scrofa (Pig)]
896 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 369 PPPHPHARIK 378 (SEQ ID NO: 27)

[Papio hamadryas (Hamadryas baboon)]
895 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 362 PPPHPHARIK 371 (SEQ ID NO: 28)

[Pan troglodytes (Chimpanzee)]
911 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 376 PPPHPHARIK 385 (SEQ ID NO: 29)

[Macaca mulatta (Rhesus macaque)]
895 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 362 PPPHPHARIK 371 (SEQ ID NO: 30)

[Cynomolgus monkey)]
895 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 362 PPPHPHARIK 371 (SEQ ID NO: 31)

FIGURE 3 (part 2 of 10)

[Homo sapiens (Human)]
919 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 377 PPPHPHARIK 386 (SEQ ID NO: 21)

[(Red squirrel)]
458 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 333 PPPHPHARIK 342 (SEQ ID NO: 32)

[Felis catus (Cat) (Felis silvestris catus)]
475 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 355 PPPHPHARIK 364 (SEQ ID NO: 33)

[Galidia elegans (Malagasy ring-tailed mongoose)]
480 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 357 PPPHPHARIK 366 (SEQ ID NO: 34)

[Eupleres goudotii (falanouc)]
475 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 350 PPPHPHARIK 359 (SEQ ID NO: 35)

[Fossa fossana (Malagasy civet) (Striped civet)]
477 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 352 PPPHPHARIK 361 (SEQ ID NO: 36)

FIGURE 3 (part 3 of 10)

[Viverricula indica (Small Indian civet)]
474 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 349 PPPHPHARIK 358 (SEQ ID NO: 37)

[Diceros bicornis (Black rhinoceros)]
461 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 337 PPPHPHARIK 346 (SEQ ID NO: 38)

[Equus caballus (Horse)]
456 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 332 PPPHPHARIK 341 (SEQ ID NO: 39)
ExPASy BLAST2 Interface 28/01/2010 18:11
http://www.expasy.ch/cgi-bin/blast.pl#A1 Page 8 of 15
Androgen receptor (Fragment)
[ar]
[Lama guanicoe pacos (Alpaca) (Lama pacos)]
467 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 342 PPPHPHARIK 351 (SEQ ID NO: 40)

[Physeter catodon (sperm whale) (Physeter macrocephalus)]
462 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 342 PPPHPHARIK 351 (SEQ ID NO: 41)

FIGURE 3 (part 4 of 10)

[trichechus manatus (Caribbeanmanatee) (West Indian manatee)]
488 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 362 PPPHPHARIK 371 (SEQ ID NO: 42)

[Elephas maximus (Indian elephant)]
469 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 344 PPPHPHARIK 353 (SEQ ID NO: 43)

[Oryctolagus cuniculus (Rabbit)]
475 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 350 PPPHPHARIK 359 (SEQ ID NO: 44)

[Lepus crawshayi]
460 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 341 PPPHPHARIK 350 (SEQ ID NO: 45)

[Tarsius bancanus (Westerntarsier) (Horsfield's tarsier)]
461 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 336 PPPHPHARIK 345 (SEQ ID NO: 46)

[Cynopterus sphinx (Indian short-nosed fruit bat)]
479 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 354 PPPHPHARIK 363 (SEQ ID NO: 47)

FIGURE 3 (part 5 of 10)

[Tupaia tana (Large tree shrew)]
470 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 358 PPPHPHARIK 367 (SEQ ID NO: 48)

[Saimiri boliviensis (Bolivian squirrel monkey)]
918 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 373 PPPHPHARIK 382 (SEQ ID NO: 49)

[Homo sapiens (Human)]
906 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 372 PPPHPHARIK 381 (SEQ ID NO: 21)

[Homo sapiens (Human)]
539 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 379 PPPHPHARIK 388 (SEQ ID NO: 21)

[Homo sapiens (Human)]
544 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 383 PPPHPHARIK 392 (SEQ ID NO: 21)

[Homo sapiens (Human)]
542 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 382 PPPHPHARIK 391 (SEQ ID NO: 21)

FIGURE 3 (part 6 of 10)

[Homo sapiens (Human)]
531 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 371 PPPHPHARIK 380 (SEQ ID NO: 21)

[Homo sapiens (Human)]
730 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 189 PPPHPHARIK 198 (SEQ ID NO: 21)

[Homo sapiens (Human)]
643 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 384 PPPHPHARIK 393 (SEQ ID NO: 21)

[Homo sapiens (Human)]
682 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 384 PPPHPHARIK 393 (SEQ ID NO: 21)

[Homo sapiens (Human)]
647 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 383 PPPHPHARIK 392 (SEQ ID NO: 21)

[Homo sapiens (Human)]
648 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 383 PPPHPHARIK 392 (SEQ ID NO: 21)

FIGURE 3 (part 7 of 10)

[Homo sapiens (Human)]
645 AA
Score = 36.7 bits (79), Expect = 0.31
Identities = 10/10 (100%), Positives = 10/10 (100%)
query: 1 PPPHPHARIK 10 (SEQ ID NO: 21)
PPPHPHARIK
Sbjct: 384 PPPHPHARIK 393 (SEQ ID NO: 21)

[Canis familiaris (Dog)]
907 AA
Score = 33.7 bits (72), Expect = 2.4
Identities = 9/10 (90%), Positives = 9/10 (90%)
query: 1 PPPHPHARIK 10 (SEQ ID NO: 21)
PPPHPH RIK
Sbjct: 380 PPPHPH (SEQ ID NO: 50)
TRIK 389

[Eulemur fulvus collaris (Collared brown lemur) (Eulemur collaris)]
884 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 359 PPHPHARIK 367 (SEQ ID NO: 51)

[Lemur catta (Ring-tailed lemur)]
458 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 335 PPHPHARIK 343 (SEQ ID NO: 52)

[Eulemur fulvus fulvus (Brown lemur)]
451 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 335 PPHPHARIK 343 (SEQ ID NO: 53)

[Hapalemur simus (Greater bamboo lemur) (Prolemur simus)]
458 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 335 PPHPHARIK 343 (SEQ ID NO: 54)

FIGURE 3 (part 8 of 10)

[Lepilemur edwardsi(Milne-Edwards's sportive lemur)]
455 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 332 PPHPHARIK 340 (SEQ ID NO: 55)

[Cheirogaleus medius (Fat-tailed dwarf lemur)]
462 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 339 PPHPHARIK 347 (SEQ ID NO: 56)

[Daubentonia madagascariensis (Aye-aye)]
464 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 333 PPHPHARIK 341 (SEQ ID NO: 57)

[Propithecus deckenii coronatus]
460 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 337 PPHPHARIK 345 (SEQ ID NO: 58)
]
[Nycticebus coucang (Slow loris)]
472 AA
Score = 33.3 bits (71), Expect = 3.3
Identities = 9/9 (100%), Positives = 9/9 (100%)
query: 2 PPHPHARIK 10 (SEQ ID NO: 21)
PPHPHARIK
Sbjct: 348 PPHPHARIK 356 (SEQ ID NO: 59)

[Cavia porcellus (Guinea pig)]
495 AA
Score = 32.9 bits (70), Expect = 4.4
Identities = 9/10 (90%), Positives = 10/10 (100%)
query: 1 PPPHPHARIK 10 (SEQ ID NO: 21)
PPPHP+ARIK
Sbjct: 370 PPPHPNARIK 379 (SEQ ID NO: 60)

FIGURE 3 (part 9 of 10)

[Rattus norvegicus (Rat)]
902 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 374 PPPTHPHARIK 384 (SEQ ID NO: 61)

[Mus musculus (Mouse)]
899 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 371 PPPTHPHARIK 381 (SEQ ID NO: 62)

[Crocuta crocuta (spotted hyena)]
912 AA
Score = 32.5 bits (69), Expect = 5.9
Identities = 9/10 (90%), Positives = 9/10 (90%)
query: 1 PPPHPHARIK 10 (SEQ ID NO: 21)
P PHPHARIK
Sbjct: 385 PPHPHARIK 394 (SEQ ID NO: 63)

[Eliurus sp. C24]
464 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 342 PPPTHPHARIK 352 (SEQ ID NO: 64)

[Steatomys sp. Gautuni]
475 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 349 PPPTHPHARIK 359 (SEQ ID NO: 65)

[Otomys angoniensis (Angoni vlei rat)]
463 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 343 PPPTHPHARIK 353 (SEQ ID NO: 66)

FIGURE 3 (part 10 of 10)

[Mus musculus (Mouse)]
899 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 371 PPPTHPHARIK 381 (SEQ ID NO: 62)

[(Silky anteater)]
467 AA
Score = 32.5 bits (69), Expect = 5.9
Identities = 10/11 (90%), Positives = 10/11 (90%), Gaps = 1/11 (9%)
query: 1 PP-PHPHARIK 10 (SEQ ID NO: 21)
PP PHPHARIK
Sbjct: 338 PPHPHPHARIK 348 (SEQ ID NO: 67)

[Procavia capensis (Cape hyrax) (Rock dassie)]
490 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 363 PPPLHPHARIK 373 (SEQ ID NO: 68)

[Didelphis marsupialis virginiana (North American opossum)]
420 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID NO: 21)
PPP HPHARIK
Sbjct: 391 PPPTHPHARIK 401 (SEQ ID NO: 69)

[Galeopterus variegatus (Malayan flying lemur) (Cynocephalus variegatus)]
453 AA
Score = 32.5 bits (69), Expect = 5.9
Identities = 10/11 (90%), Positives = 10/11 (90%), Gaps = 1/11 (9%)
query: 1 PPPH-PHARIK 10 (SEQ ID NO: 21)
PPPH PHARIK
Sbjct: 327 PPPHHPHARIK 337 (SEQ ID NO: 70)

METHOD OF TREATING ENDOMETRIOSIS

RELATED APPLICATIONS

This application is the U.S. National Stage of International Application No. PCT/GB2012/052722, filed on Nov. 1, 2012, which designates the U.S., published in English, and claims priority under 35 U.S.C. § 119 or 365(c) to GB Application No. 1118831.5, filed Nov. 1, 2011.

INCORPORATION BY REFERENCE OF MATERIAL IN ASCII TEXT FILE

This application incorporates by reference the Sequence Listing contained in the following ASCII text file being submitted concurrently herewith:

a) File name: 44751021000SeqListing.txt; created Oct. 12, 2017, 13.0 KB in size.

The present invention relates to a medical use of molecules, and in particular the use of molecules to treat conditions in which an activity of the androgen receptor (AR) and/or estradiol receptor (ER) is a contributory factor.

The listing or discussion of an apparently prior-published document in this specification should not necessarily be taken as an acknowledgement that the document is part of the state of the art or is common general knowledge.

Endometriosis is a prevalent disease in women of reproductive age, wherein cells from the lining of the uterus appear and flourish outside the uterine cavity, most commonly on the ovaries. It has a propensity to run a chronic and recurrent course after treatment, leading to debilitating chronic pelvic pain and infertility. It is the leading cause of admission to hospital for abdominal pain and infertility, and is believed to occur in 5-10% of woman.

Current methods for treating endometriosis suffer from numerous drawbacks.

Non-steroidal anti-inflammatories (NSAIDs) such as ibuprofen and naproxen treat inflammation caused by endometriosis as well as easing pain and discomfort; however they can cause nausea, vomiting and diarrhea. Long term use may also result in gastrointestinal irritation, kidney damage and increased risk of heart attack and stroke, and it can reduce the efficacy of aspirin in reducing adverse cardiovascular events. When taken with quinolone-based antibiotics, NSAIDs can induce seizures.

Paracetamol and codeine (either alone or with paracetamol) may be prescribed to endometriosis patients, but can often lead to constipation which may aggravate symptoms.

The mainstay of management of endometriosis symptoms since the late 1950s has been the combined oral contraceptive pill. Although not curative, the pill is generally well tolerated and does alleviate the main symptoms of pain by suppressing the menstrual cycle. The treatment regimen varies from a three week on/one week off cycle normally used for contraception to a three to four month on/one week off cycle in the case of severe disease. Common side effects include irregular vaginal bleeding, fluid retention, abdominal bloating, weight gain, increased appetite, nausea, headaches, breast tenderness and depression. A significant disadvantage is the contraceptive effect and so the contraceptive pill is not suited for women who wish to preserve fertility.

Synthetic progesterone (e.g. progestin/progestogens) prevents ovulation and has been used successfully to treat endometriosis since the mid 1950s, for example as an intrauterine device (e.g. the Mirena IUD). As well as the obvious contraceptive effect however, other side effects include mood changes, bloating, irregular bleeding and weight gain.

Anti-progestogens such as synthetic testosterone derivatives (e.g. Danzol and Gestrinone) have been used to induce a menopausal like state by decreasing natural estrogen and progesterone levels; however they can induce weight gain, acne, hair growth and voice deepening.

Gonadotropin-releasing hormone (GnRH) analogues (e.g. Goserelin, Nafarelin, Leuprorelin/Leupron and Triptorelin) also induce an artificial menopausal state by blocking estrogen production. However, common side effects include hot flushes, vaginal dryness and low libido. Long term use, for example longer than six months, is associated with bone loss leading to osteoporosis.

More recently, the use of aramatase inhibitors (e.g. letrozole and anastrozole) that block the conversion of testosterone to estrogen, has been explored in combination with GnRH agonists which are necessary to prevent overstimulation of the ovaries and development of ovarian cysts in pre-menopausal women. However, calcium, vitamin D and bisphosphonates are required to alleviate bone loss associated with extended therapy.

Three main types of surgical intervention can be employed to combat endometriosis. First, keyhole Laparoscopy may be used where heat, laser or electro-ablation removes lesions, often during a diagnostic procedure. Typical time to laproscopic examination can exceed eight years and symptoms frequently recur due to incomplete removal of lesions and/or failure to identify hidden lesions. Second, a laparotomy may be performed to gain access to the abdominal cavity; however, this is a major surgical intervention with associated risks and prolonged hospital stay. The third and final option is a hysterectomy but even this is not curative and lesions may return, especially if the ovaries are left in place.

Ngô et al (*J Pathol* 2010; 222: 148-157) discuss the potential of controlling the progression of endometriosis in vitro and in vivo, and identify the ERK pathway as a new target to treat endometriosis. However, the authors stress that further clinical studies are required to evaluate the effects and tolerability in humans, and no mention is made about preserving fertility.

Accordingly, there remains a need to treat endometriosis, and/or other conditions in which an activity of the AR and/or ER is a contributory factor, in a way that preserves fertility, and which preferably suffers from less drawbacks than those above.

Surprisingly and unexpectedly, the inventors have now demonstrated that reducing the interaction between the tyrosine kinase Src and either the AR or ER can provide symptomatic relief for endometriosis patients, and at the same time, has no contraceptive effect.

Both the AR and ER are known to interact with the tyrosine kinase Src and potentially other Src-family kinases. The AR receptor binds to the SH3 domain of Src (Migliaccio et al (Oncogene 2007, 26: 6619)). SH3 domains are 50-70 amino acids long and often feature in eukaryotic signal transduction and cytoskeletal proteins. The domains bind proline rich peptides and thereby play a major role in regulation of kinase activity as well as localisation and substrate recognition. The ER receptor binds to the SH2 domain of Src (Migliaccio et al (Cancer Research 2005, 65(22):10585-93)). SH2 domains are generally around 100 amino acids long and typically bind to a phosphorylated tyrosine residue in the context of a longer peptide motif in a target protein.

Without wishing to be bound by any theory, the inventors believe that by reducing the interaction between a Src family kinase and either AR or ER, the non-genomic regulation of signal transduction by steroid hormones can be selectively inhibited (e.g. activation of a Src family kinase signalling, cyclin D1 expression and DNA synthesis), while at the same time the genomic regulation of signal transcription by steroid hormones is retained. In this way, many of the side effects associated with conventional steroid hormone blockade or ablation (which abolish both genomic and non-genomic effects) are avoided, and treatment can be more sustained. Furthermore, the inventors have found that reducing the interaction between a Src family kinase and either AR or ER is, surprisingly, without a contraceptive effect. This is in sharp contrast to existing treatments. Preservation of fertility represents a significant advancement in endometriosis treatment since, currently, treatment with anti-androgens and/or anti-estrogens must be suspended to allow conception, which suspension can lead to disease recurrence. Thus, the inventors believe that targeting this interaction will be useful in combating endometriosis and/or other conditions in which an activity of the AR and/or ER plays a role.

Accordingly, a first aspect of the invention provides a molecule that inhibits or prevents an interaction between a Src family kinase and an AR or ER, for use in preventing or treating a non-cancerous condition in which an activity of AR and/or ER is a contributory factor in a subject, or for use in preventing or treating a cancerous condition in which an activity of AR and/or ER is a contributory factor in a subject who wishes to preserve fertility, or for use in preventing or treating a gynaecological condition in which an activity of AR and/or ER is a contributory factor in a subject.

Similarly, the invention provides the use of a molecule that inhibits or prevents an interaction between a Src family kinase and an AR or ER in the manufacture of a medicament for preventing or treating a non-cancerous condition in which an activity of AR and/or ER is a contributory factor in a subject, or for preventing or treating a cancerous condition in which an activity of AR and/or ER is a contributory factor in a subject who wishes to preserve fertility, or for preventing or treating a gynaecological condition in which an activity of AR and/or ER is a contributory factor in a subject.

Similarly, the invention provides a method of preventing or treating a non-cancerous condition in which an activity of an AR and/or ER is a contributory factor in a subject, or for preventing or treating a cancerous condition in which an activity of AR and/or ER is a contributory factor in a subject who wishes to preserve fertility, or for preventing or treating a gynaecological condition in which an activity of AR and/or ER is a contributory factor in a subject, the method comprising administering to a subject in need thereof an effective amount of a molecule that inhibits or prevents an interaction between a Src family kinase and an AR or ER.

By "preventing or treating" a condition in which an activity of AR and/or ER is a contributory factor we include the meaning that the invention can be used to alleviate symptoms of the disorder (i.e. palliative use), or to treat the disorder (e.g. by inhibition or elimination of the causative agent), or to prevent the disorder (i.e. prophylactic use—either preventing the symptoms from worsening or progressing, or reducing the progression of a disorder).

Preferably, the condition in which an activity of AR and/or ER is a contributory factor is prevented or treated in a mammalian subject such as a human. Alternatively, the subject may be an animal, for example a domesticated animal (for example a dog or cat), laboratory animal (for example laboratory rodent, mouse, rat or rabbit) or an animal important in agriculture (i.e. livestock), for example, cattle, sheep, horses or goats. The subject may be female or male.

By a Src family kinase we include any kinase of the Src family. For example, the kinase may be any non-tyrosine kinase selected from Src, Yes, Fyn and Fgr (i.e. a kinase of the SrcA subfamily), Lck, Hck, Blk, and Lyn (i.e. a kinase of the SrcB subfamily) and Frk (Amanchy et al, Proteome Res 2008, 7(8): 3447). Most preferably, the Src family kinase is Src kinase.

By a Src family kinase we include the meaning of a human Src family kinase such as human Src kinase, by androgen receptor (AR) we include the meaning of human AR, and by estradiol receptor (ER) we include the meaning of human ER, the sequences of all of which are provided in Migliaccio et al (Cancer Research 2005, 65(22):10585-93), Migliaccio et al (Oncogene 2007, 26: 6619), Venter et al (Science 2001, 291(5507):1304-51) and WO 2008/113770. It will be appreciated that there is natural variability with respect to the gene and mRNA sequences, and such variability is included within the meaning of each of a Src family kinase (e.g. Src kinase), AR and ER as herein defined.

Variants of human Src family kinase (e.g. Src kinase), AR and/or ER are also included provided that they share one or more activities of the parent Src family kinase (e.g. Src kinase), AR or ER. In other words, the variants are functional variants. For example, the variants may share at least 60% sequence identity, for example at least 65%, 70%, 75%, 80% and 85% sequence identity and more preferably 90%, 95% or 99% sequence identity with the corresponding human sequence. Variations include insertions, deletions and substitutions, either conservative or non-conservative. By "conservative substitutions" is intended combinations such as Gly, Ala; Val, Ile, Leu; Asp, Glu; Asn, Gln; Ser, Thr; Lys, Arg; and Phe, Tyr By each of a Src family kinase (e.g. Src kinase), AR and ER, we also include orthologues of human Src family kinase (e.g. Src kinase), AR and ER. Examples of suitable homologous Src family kinases, AR and ER include those from mice and rats. Other orthologues include those from the species listed in FIG. 3. It will be appreciated that there is natural variability with respect to the gene and mRNA sequences encoding the orthologues of each of human Src family kinase, AR and ER, and that this variability is included within the meaning of a homologous Src family kinase, AR and ER as defined.

In an embodiment, the molecule is one that inhibits or prevents an interaction between the SH3 domain of a Src family kinase (e.g. Src kinase) and an androgen receptor. The details of this interaction are provided in Migliaccio et al (Oncogene 2007, 26: 6619).

By the SH3 domain' of a Src family kinase we include the meaning of the N-terminal Src homology-3 domain of a Src family kinase (e.g. Src kinase). SH3 domains are typically 50-70 amino acids long and bind proline rich peptides. Work by Migliaccio et al (*EMBO J* 2000, 19: 5406-5417) has demonstrated the importance of the SH3 domain of Src kinase in its interaction with AR.

In another embodiment, the molecule is one that inhibits or prevents an interaction between the SH2 domain of a Src family kinase (e.g. Src kinase) and an estradiol receptor. The details of this interaction are provided in Migliaccio et al (Cancer Research 2005, 65(22):10585-93).

By the SH2 domain' of a Src family kinase we include the meaning of the Src homology-2 domain of a Src family kinase (e.g. Src kinase). SH2 domains are generally around 100 amino acids in length and typically bind to phosphorylated tyrosine residues.

With respect to the mammalian subject which is to be treated, it is appreciated that the molecule is one which that can inhibit or prevent the interaction between a Src family kinase (e.g. Src kinase) and an androgen or estradiol receptor, of that mammalian species. For example, when the mammalian subject is a human the molecule can inhibit or prevent the interaction between a human Src family kinase (e.g. Src kinase) and either human AR or human ER, and so on.

By a molecule that prevents or inhibits the interaction between a Src family kinase and AR or ER, we include both the meaning of prohibiting an interaction from forming in the first place and reducing an interaction once it has been formed. Preferably, the molecule prohibits or reduces the interaction to an undetectable level.

In a preferred embodiment, the molecule prevents or inhibits the interaction between a Src family kinase (e.g. Src kinase) and AR or ER, selectively. For example, it is preferred if the molecule prevents or inhibits an interaction between a Src family kinase and AR or ER to a greater extent (e.g. at least 5 fold, 10 fold, 20 fold, 50 fold, 100 fold or 1000 fold) than it prevents interactions between a Src family kinase and any other molecule. Likewise, it is preferred if the molecule prevents or inhibits an interaction between AR or ER, and a Src family kinase to a greater extent (e.g. at least 5 fold, 10 fold, 20 fold, 50 fold, 100 fold or 1000 fold) than it prevents the interactions between AR or ER, and any other molecule.

Whether or not a molecule prevents or inhibits the interaction between a Src family kinase and AR or ER, is conveniently determined by assessing the interaction between a Src family kinase and either AR or ER, in the presence and absence of the particular molecule. As mentioned above, the SH3 domain of Src kinase is believed to mediate an interaction between Src kinase and AR, and so the interaction between the SH3 domain of a Src family kinase (e.g. Src kinase) and AR may be assessed in the presence and absence of the particular molecule. Similarly, the SH2 domain of Src kinase is believed to mediate an interaction between Src kinase and ER, and so the interaction between the SH2 domain of a Src family kinase (e.g. Src kinase) and ER may be assessed in the presence and absence of the particular molecule. Methods for assessing the interaction between two proteins are well known in the art and any suitable method may be used. Examples include enzyme linked immunosorbent assays (ELISA), surface plasmon resonance assays, competition assays, chip-based assays, immunocytofluorescence, yeast two-hybrid technology and phage display, all of which are common practice in the art and are described, for example, in Plant et al (1995) *Analyt Biochem,* 226(2), 342-348. and Sambrook et al (2001) Molecular Cloning A Laboratory Manual. Third Edition. Cold Spring Harbor Laboratory Press, Cold Spring Harbor, N.Y. Other methods of assessing protein interactions include ultrafiltration with ion spray mass spectroscopy/HPLC methods or other physical and analytical methods. Fluorescence Energy Resonance Transfer (FRET) methods, for example, are well known to those skilled in the art, may be used, in which binding of two fluorescent labelled entities may be measured by measuring the interaction of the fluorescent labels when in close proximity to each other. In a particularly preferred embodiment, an immunoprecipitation assay such as that described in Migliaccio et al (*Oncogene* 2007, 26: 6619) is used to assess the interaction between the SH3 domain of a Src family kinase (e.g. Src kinase) and AR, and/or the interaction between the SH2 domain of a Src family kinase (e.g. Src kinase) and ER.

In a preferred embodiment, the molecule is one that comprises or consists of the structure:

$B_j$-[$(Pro)_n$-$X_r$-His-Pro-His-Ala-Arg-Ile-Lys]$_m$$R_p$, (SEQ ID NO: 1) or $B_j$-[lys-ile-arg-ala-his-pro-his-$x_r$-$(pro)_n$]$_m$$R_p$ (SEQ ID NO: 2), or a derivative or fragment thereof, wherein B is a first chemical moiety, j is 0 or 1, n is an integer from 1-10, X is any amino acid, r is an integer from 0 to 2, m is an integer from 1 to 3, R is a second chemical moiety, p is 0 or 1, and [lys-ile-arg-ala-his-pro-his-$x_r$-$(pro)_n$] (SEQ ID NO: 2) is the retro-inverso peptide of [$(Pro)_n$-$X_r$-His-Pro-His-Ala-Arg-Ile-Lys] (SEQ ID NO: 1).

It will be understood that the molecule that comprises or consists of the structure $B_j$-[$(Pro)_n$-$X_r$-His-Pro-His-Ala-Arg-Ile-Lys]$_m$-$R_p$, (SEQ ID NO: 1) or $B_j$-[lys-ile-arg-ala-his-pro-his-$x_r$-$(pro)_n$]$_m$-$R_p$ (SEQ ID NO: 2) generally has a peptide portion [$(Pro)_n$-$X_r$-His-Pro-His-Ala-Arg-Ile-Lys]$_m$ (SEQ ID NO: 1) or [lys-ile-arg-ala-his-pro-his-$x_r$-$(pro)_n$]$_m$ (SEQ ID NO: 2), and optionally further chemical moieties at one or both termini (i.e. $B_j$ and $R_p$). In other words, j=0 and p=0; or j=1 and p=0; or j=0 and p=1; or j=1 and p=1. In an embodiment, j=0 and p=0 such that the molecule is a peptide with the structure [$(Pro)_n$-$X_r$-His-Pro-His-Ala-Arg-Ile-Lys]$_m$ (SEQ ID NO: 1) or [lys-ile-arg-ala-his-pro-his-$x_r$-$(pro)_n$]$_m$ (SEQ ID NO: 2).

B and R may be independently, any chemical moiety such as any of a lipid (e.g. a glycolipid, phospholipid, sphingolipid), a fatty acid, a triglyceride, glycerol, a prenyl or iso-prenyl moiety (e.g. farnesyl or geranyl geranyl moieties), a carbohydrate (e.g. mono- and poly-saccharides), an amino acid, a peptide, a polypeptide or a nucleic acid, or a combination thereof. Thus, the moiety may be a glycopeptides or a lipo-peptide. The moiety may be a low or high molecular weight polyethylene glycol, for example with a molecular weight ranging from 200-70000. Any additional suitable moiety may be determined by a skilled person.

In an embodiment, B is any of H, or an acetyl group, or one or a sequence of amino acids provided with a free or acetyl-derivatised $NH_2$ group.

In a further embodiment, R is any of an OH group, or an $NH_2$ group or one or a sequence of amino acids with a C-terminal carboxy-amide group.

Chemical moieties B and R may be optionally attached to the peptide portion of the molecule such that they may be cleaved off the peptide portion when the molecule is administered to the subject. For example, either of moieties B and R may comprise a cleavage site that is capable of being cleaved when the molecule is administered to the body. Generally, the cleavage site is a protease cleavage site that is capable of being cleaved by a protease that resides in the subject.

Chemical moieties B and/or R may be joined to the peptide portion by any suitable method known in the art. For example, moieties B and/or R may be joined to the peptide portion by any of the conventional ways of cross-linking polypeptides, such as those generally described in O'Sullivan et al *Anal. Biochem.* (1979) 100, 100-108. For example, the first portion may be enriched with thiol groups and the second portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP), a heterobifunctional cross-linking agent which incorporates a disulphide bridge between the conjugated species. Amide and thioether bonds, for example achieved with m-maleimidobenzoyl-N-hydroxysuccinimide ester, are generally more stable in vivo than disulphide bonds.

Further useful cross-linking agents include S-acetylthioglycolic acid N-hydroxysuccinimide ester (SATA) which is a thiolating reagent for primary amines which allows deprotection of the sulphydryl group under mild conditions (Julian et al (1983) *Anal. Biochem.* 132, 68), dimethylsuberimidate dihydrochloride and N,N'-o-phenylenedimaleimide.

Further ways of joining chemical moieties B and/or R to the peptide portion include a chemical ligation protocol, a protocol for coupling using click chemistry or by using a protocol for coupling using Staudinger ligation, which are well known in the art. Other suitable methods may be determined by the skilled person.

When chemical moieties B and/or R are peptides or polypeptides, it is appreciated that the peptide portion of the molecule and chemical moieties B and/or R may be part of a fusion polypeptide that may be encoded by a nucleic acid molecule. For example, chemical moiety B and/or R may be genetically engineered to contain the peptide portion of the molecule using genetic engineering techniques well established in the art.

Conveniently, the peptide portion $[(Pro)_n-X_r$-His-Pro-His-Ala-Arg-Ile-Lys$]_m$ (SEQ ID NO: 1) or [lys-ile-arg-ala-his-pro-his-$x_r-(pro)_n]_m$ (SEQ ID NO: 2) of the molecule is less than 57 amino acid residues in length, such as less than 55, 50, 45, 40, 35, 30, 25, 20 or 15 amino acids in length. Thus, the peptide portion may have a length of from 8 to 60 amino acid resides, or a length from 10 to 15 amino acid residues, or a length of from 15 to 20 amino acid residues, or a length of from 20 to 25 amino acid residues, or a length of from 25 to 30 amino acid residues, or a length of from 30 to 35 amino acid residues, or a length of from 35 to 40 amino acid residues, or a length of from 40 to 45 amino acid residues, or a length of from 45 to 50 amino acid residues, or a length of from 50 to 55 amino acid residues. Preferably, the peptide portion is 8, 9, 10, 11, 12, 13, 14, 15, 16, 17, 18, 19, 20, 21, 22, 23, 24 or 25 amino acids in length, and most preferably 10 amino acids in length.

It is understood that a fragment of the molecule comprising or consisting of the structure $B_j-[(Pro)_n-X_r$-His-Pro-His-Ala-Arg-Ile-Lys$]_m-R_p$ (SEQ ID NO: 1), or $B_j$-[lys-ile-arg-ala-his-pro-his-$x_r-(pro)_n]_m-R_p$ (SEQ ID NO: 2), may be used provided that it is capable of preventing or inhibiting an interaction between a Src family kinase (e.g. Src kinase) and AR and/or ER. Thus, it is possible that the molecule may contain fewer than the 8 amino acids mentioned above. Typically, the fragment is a fragment of the peptide portion $[(Pro)_n-X_r$-His-Pro-His-Ala-Arg-Ile-Lys$]_m$ (SEQ ID NO: 1) or [lys-ile-arg-ala-his-pro-his-$x_r-(pro)_n]_m$ (SEQ ID NO: 2) of the molecule, and generally is at least 3 amino acids in length, such as at least 4, 5, 6, 7, 8, 9, 10, 11, 12, 13, 14 or 15 amino acids in length. Thus, the molecule may comprise or consist of a fragment of the peptide $[(Pro)_n-X_r$-His-Pro-His-Ala-Arg-Ile-Lys$]_m$ (SEQ ID NO: 1) or [lys-ile-arg-ala-his-pro-his-$x_r-(pro)_n]_m$. (SEQ ID NO: 2) provided that it is capable of preventing or inhibiting an interaction between a Src family kinase (e.g. Src kinase) and AR and/or ER.

A derivative or salt of the fragment may be used as described further below. For example, capping moieties may be added to one or both ends of the fragment to improve stability.

Examples of suitable fragments may be selected from the group consisting of: HPHARIK (SEQ ID NO: 3), HPHAR (SEQ ID NO: 4), PHPHAR (SEQ ID NO: 5), HPH, PHPH (SEQ ID NO: 6), PPHPH (SEQ ID NO: 7), PPPHPH (SEQ ID NO: 8), PHP, PPHP (SEQ ID NO: 9), PPPHP (SEQ ID NO: 10), PPPH (SEQ ID NO: 11), PPH, and PPP. Particular derivatives or salts of the fragments may be selected from the group consisting of: Ac-HPHARIK-NH2 (SEQ ID NO: 12), Ac-HPHAR-NH2 (SEQ ID NO: 13), Ac-PHPHAR-NH2 (SEQ ID NO: 14), Ac-HPH-NH2, Ac-PHPH-NH2 (SEQ ID NO: 15), Ac-PPHPH-NH2 (SEQ ID NO: 16), Ac-PPPHPH-NH2 (SEQ ID NO: 17), Ac-PHP-NH2, Ac-PPHP-NH2 (SEQ ID NO: 18), Ac-PPPHP-NH2P (SEQ ID NO: 19), Ac-PPPH-NH2 (SEQ ID NO: 20), Ac-PPH-NH2 and Ac-PPP-NH2.

It is appreciated that when moieties B and/or R are peptides, the entire molecule may be a peptide and such a peptide may be more than 57 amino acids in length. However, if the entire molecule is a peptide, it is preferred if it is less than 150 amino acids in length, such as less than 140, 130, 120, 110, 100, 90, 80, 70 or 60 amino acids in length.

Generally, the molecule has a molecular weight of less than 50 kDa such as less than 40, 30, 20, 10 or 5 kDa. Typically, the molecule is between 1000 and 5000 Da in molecular weight. Thus, the molecule may be about 4500, 4000, 3500, 3000 or 2500 Da in molecular weight, or weigh between 1000 and 2500 Da in molecular weight.

In one embodiment, n is any of 1, 2, 3, 4, 5, 6, 7, 8, 9 or 10, and most preferably, n=3. In another embodiment, m is any of 1, 2 or 3, and most preferably, m=1. Thus, in a particularly preferred embodiment, n is 3 and m is 1.

$X_r$ represents a stretch of 1 or 2 amino acid residues which can, independently or both, be any amino acid residue. Thus, the amino acid residues represented by $X_r$ may be a any naturally occurring amino acid residue which is encoded by DNA, selected from alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y) and valine (Val, V). However, other than when the peptide portion is made by expression from a polynucleotide, the amino acid residues represented by $X_r$ may comprise one or more amino acid residues which are not encoded by DNA, including those described below. In one embodiment r is 0 and in an alternative embodiment r is 1 and X is a threonine residue.

For the avoidance of doubt, the molecule is not AR or ER.

Without wishing to be bound by any theory, the inventor believes that the peptide PPPHPHARIK (SEQ ID NO: 21) is the portion of human AR that mediates the interaction with the SH3 domain of a Src family kinase. Thus, in a particularly preferred embodiment, the peptide portion $[(Pro)_n-X_r$-His-Pro-His-Ala-Arg-Ile-Lys$]_m$ (SEQ ID NO: 1) or [lys-ile-arg-ala-his-pro-his-$x_r-(pro)_n]_m$ (SEQ ID NO: 2) of the molecule is PPPHPHARIK (SEQ ID NO: 21) or the retro-inverso peptide thereof, kirahphppp (SEQ ID NO: 22).

The peptide PPPHPHARIK (SEQ ID NO: 21) is equivalent to amino acid residues 377-386 of human AR and, without wishing to be bound by any theory, it is believed by the inventor that the corresponding portions of AR from other species would share the same activity. By "corresponding portion" we include the meaning of the amino acid residue sequence in another AR which aligns to the given amino acid sequence in human AR when the human AR and the other AR are compared, for example by using an alignment tool such as MacVector or CLUSTALW. Thus, in another preferred embodiment, the peptide portion is a peptide that corresponds to the amino acid sequence at positions 377-386 (PPPHPHARIK (SEQ ID NO: 21)) of the human AR. For example, the corresponding peptide in mouse and rat AR is PPTHPHARIK (SEQ ID NOs: 23 and 25), and so the peptide portion may be PPTHPHARIK or the retro-inverso peptide thereof, kirahphtpp (SEQ ID NOs: 24 and 26). The corresponding peptides in a selection of other species are provided in FIG. 3, and so the peptide portion may be any of the peptides listed in FIG. 3 or the retro-inverso peptides thereof. Preferably, the peptide PPPHPHARIK (SEQ ID NO: 21) is administered to human subjects, and the peptide PPTHPHARIK (SEQ ID NOs: 23 and 25) is administered to mouse or rat subjects, and so on.

Aligning two proteins may be carried out using the Clustal W program (Thompson et al., 1994). The parameters used may be as follows: Fast pairwise alignment parameters: K-tuple(word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

In a particularly preferred embodiment, the molecule comprises or consists of the peptide PPPHPHARIK (SEQ ID NO: 21) or PPTHPHARIK (SEQ ID NO: 23).

The peptide portion $[(Pro)_n$-$X_r$-His-Pro-His-Ala-Arg-Ile-Lys$]_m$, (SEQ ID NO: 1) or [lys-ile-arg-ala-his-pro-his-$x_r$-$(pro)_n]_m$ (SEQ ID NO: 2) or fragment thereof of the molecule defined above is typically made using protein chemistry techniques for example using partial proteolysis (either exolytically or endolytically), or by de novo synthesis. Alternatively, the peptides may be made by recombinant DNA technology. Suitable techniques for cloning, manipulation, modification and expression of nucleic acids, and purification of expressed proteins, are well known in the art and are described for example in Sambrook et al (2001) "*Molecular Cloning, a Laboratory Manual*", 3rd edition, Sambrook et al (eds), Cold Spring Harbor Laboratory Press, Cold Spring Harbor, N.Y., USA.

The peptide portion $[(Pro)_n$-$X_r$-His-Pro-His-Ala-Arg-Ile-Lys$]_m$ (SEQ ID NO: 1) or [lys-ile-arg-ala-his-pro-his-$x_r$-$(pro)_n]_m$ (SEQ ID NO: 2) or fragment thereof of the molecule defined above can also be chemically synthesised, for example, by the solid phase peptide synthesis of Merrifield et al (1964). Alternatively, the peptide portion can be synthesised using standard solution methods (see, for example, Bodanszky, 1984 and Dugas et al, 1981). Newly synthesised peptides can be purified, for example, by high performance liquid chromatography (HPLC), and can be characterised using, for example, mass spectrometry or amino acid sequence analysis.

It will be appreciated that other suitable molecules may include any antibody, either against a Src family kinase (e.g. Src kinase), or either of AR and ER, that is capable of preventing or inhibiting the interaction between a Src family kinase (e.g. Src kinase) and AR or ER. As mentioned earlier, the inventor believes that the SH3 domain of Src kinase and amino acid residues 377-386 of AR mediate the interaction between Src kinase and AR. Thus, it will be understood that suitable molecules that inhibit or prevent an interaction between a Src family kinase (e.g. Src kinase) and either AR or ER include an antibody against the SH3 domain of a Src family kinase (e.g. Src kinase) or an antibody that binds to AR at a position that corresponds to amino acids 377-386 of the human AR (e.g. an antibody against a peptide having the structure $(Pro)_n$-$X_r$-His-Pro-His-Ala-Arg-Ile-Lys (SEQ ID NO: 1), where n is an integer from 1-10, X is any amino acid and r is an integer from 0 to 2, such as an antibody against PPPHPHARIK (SEQ ID NO: 21) or PPTHPHARIK (SEQ ID NO: 23)). Similarly, the SH2 domain of Src kinase is believed to mediate the interaction between Src kinase and ER. Thus, it will be understood that suitable molecules that inhibit or prevent an interaction between a Src family kinase (e.g. Src kinase) and either AR or ER include an antibody against the SH2 domain of a Src family kinase (e.g. Src kinase). Preferably, the antibody prevents or inhibits the interaction between a Src family kinase (e.g. Src kinase) and AR or ER, selectively, as discussed above.

As used herein, the term "antibody" includes but is not limited to polyclonal, monoclonal, chimeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. Also included are domain antibodies (dAbs), diabodies, camelid antibodies and engineered camelid antibodies. Furthermore, for administration to humans, the antibodies and fragments thereof may be humanised antibodies, which are now well known in the art (Janeway et al (2001) *Immunobiology.*, 5th ed., Garland Publishing).

Suitable antibodies described above that bind to particular regions of a Src family kinase (e.g. Src kinase) or AR and ER, can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. *Nature* 256: 495-497); antibody phage display (Winter et al (1994) "Making antibodies by phage display technology." *Annu. Rev. Immunol.* 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni et al (2001) "Isolation of anti-angiogenesis antibodies from a large combinatorial repertoire by colony filter screening." *Nucleic Acids Res.* 29: E27). Further, antibodies and antibody fragments suitable for use in the present invention are described, for example, in the following publications: *"Monoclonal Hybridoma Antibodies: Techniques and Application*", Hurrell (CRC Press, 1982); *"Monoclonal Antibodies: A Manual of Techniques*", H. Zola, CRC Press, 1987, ISBN: 0-84936-476-0; *"Antibodies: A Laboratory Manual*" 1st Edition, Harlow & Lane, Eds, Cold Spring Harbor Laboratory Press, New York, 1988. ISBN 0-87969-314-2; *"Using Antibodies: A Laboratory Manual*" 2nd Edition, Harlow & Lane, Eds, Cold Spring Harbor Laboratory Press, New York, 1999. ISBN 0-87969-543-9; and "*Handbook of Therapeutic Antibodies*" Stefan Dübel, Ed., 1st Edition, —Wiley-VCH, Weinheim, 2007. ISBN: 3-527-31453-9.

It is appreciated that the molecule of the invention may comprise the sequence of a cell-penetrating peptide (also known as a protein transduction domain) that facilitates entry into cells. As is well known in the art, cell-penetrating peptides are generally short peptides of up to 30 residues having a net positive charge and act in a receptor-independent and energy-independent manner (Lindgren et al, 2000; Deshayes et al, 2005a and 2005b; Takeuchi et al, 2006, the entire disclosure of which relating to cell-penetrating peptides is incorporated herein by reference). Thus, either of chemical moieties B and R mentioned above, may be a cell-penetrating peptide. If so, the cell-penetrating peptide is preferably cleavable from the portion of the molecule responsible for inhibiting or preventing an interaction between a Src family kinase (e.g. Src kinase) and AR or ER. For example, it may be cleavable inside a cell.

The molecule may also be modified so that it can be more easily detected, for example by biotinylating it or by incorporating any detectable label known in the art such as radiolabels, fluorescent labels or enzymatic labels.

The amino acid residues of the molecules described herein may be in the "L" isomeric form. However, residues in the "D" isomeric form can be substituted for any L-amino acid residue, as long as the molecules can still inhibit or prevent an interaction between a Src family kinase (e.g. Src kinase) and AR or ER. This definition includes, unless otherwise specifically indicated, chemically-modified amino acids, including amino acid analogues (such as penicillamine, 3-mercapto-D-valine), naturally-occurring non-proteogenic amino acids (such as norleucine), and chemically-synthesised compounds that have properties known in the art to be characteristic of an amino acid. The term "proteogenic" indicates that the amino acid can be incorporated into a protein in a cell through well-known metabolic pathways.

Thus, in one embodiment, the peptide portion of the molecule above is the retro-inverso peptide of the peptide $[(Pro)_n$-$X_r$-His-Pro-His-Ala-Arg-Ile-Lys$]_m$ (SEQ ID NO: 1) or a fragment thereof (preferences for which include those defined above). By retro-inverso peptide (also known as all-D-retro or retro-enantio peptides) we include the meaning of a peptide in which all of the L-amino acids are replaced with D-amino acids and the peptide bonds are reversed. Thus, the peptides are composed of D-amino acids assembled in the reverse order from that of the parent L-sequence. The retro-inverso peptide of $[(Pro)_n$-$X_r$-His-Pro-His-Ala-Arg-Ile-Lys$]_m$, (SEQ ID NO: 1) is [lys-ile-arg-ala-his-pro-his-$x_r$-$(pro)_n]_m$ (SEQ ID NO: 2) (where lower-case letters denote the corresponding D-amino acids). Retro-inverso peptides can be synthesised by methods known in the art, for example such as those described in Meziere et al (1997) *J Immunol.* 159 3230-3237. This approach involves making pseudopeptides containing changes involving the backbone, and not the orientation of side chains which remain very similar to the parent peptide. Retro-inverse peptides are much more resistant to proteolysis.

For the avoidance of doubt, all of the preferences indicated above for $X_r$, also apply to its corresponding D-amino acid $x_r$.

The peptide portion of the molecule described above can be a peptide "mimetic", i.e. peptidomimetics which mimic the structural features of the peptide comprising or consisting of the amino acid sequence as described above.

Peptidomimetics that are non-peptide in nature can be designed and synthesised by standard organic chemical methods. Peptidomimetics that are non-peptide in nature can be even more advantageous in therapeutic use, in the resistance to degradation, in permeability and in possible oral administration.

Peptidomimetics are small molecules that can bind to proteins by mimicking certain structural aspects of peptides and proteins. They are used extensively in science and medicine as agonists and antagonists of protein and peptide ligands of cellular and other receptors, and as substrates and substrate analogues for enzymes. Some examples are morphine alkaloids (naturally-occurring endorphin analogues), penicillins (semi-synthetic), and HIV protease inhibitors (synthetic). Such compounds have structural features that mimic a peptide or a protein and as such are recognised and bound by other proteins. Binding the peptidomimetic either induces the binding protein to carry out the normal function caused by such binding (agonist) or disrupts such function (antagonist, inhibitor).

A primary goal in the design of peptide mimetics has been to reduce the susceptibility of mimetics to cleavage and inactivation by peptidases. In one approach, such as disclosed by Sherman et al (1990), one or more amide bonds have been replaced in an essentially isosteric manner by a variety of chemical functional groups. This stepwise approach has met with some success in that active analogues have been obtained. In some instances, these analogues have been shown to possess longer biological half-lives than their naturally-occurring counterparts. In another approach, a variety of uncoded or modified amino acids such as D-amino acids and N-methyl amino acids have been used to modify mammalian peptides. Alternatively, a presumed bioactive conformation has been stabilised by a covalent modification, such as cyclization or by incorporation of γ-lactam or other types of bridges (Veber et al, 1978) and Thorsett et al, 1983). Another approach, disclosed by Rich (1986) has been to design peptide mimics through the application of the transition state analogue concept in enzyme inhibitor design. For example, it is known that the secondary alcohol of statine mimics the tetrahedral transition state of the sessile amide bond of the pepsin substrate.

In U.S. Pat. No. 5,552,534, non-peptide compounds are disclosed which mimic or inhibit the chemical and/or biological activity of a variety of peptides. Such compounds can be produced by appending to certain core species, such as the tetrahydropyranyl ring, chemical functional groups which cause the compounds to be at least partially cross-reactive with the peptide. Other techniques for preparing peptidomimetics are disclosed in U.S. Pat. No. 5,550,251 and U.S. Pat. No. 5,288,707.

Commercially available software packages can be used to design small peptides and/or peptidomimetics, preferably non-hydrolysable analogues, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

It is appreciated that a salt or derivative of the molecule described herein may be useful to prevent or treat a condition in which an activity of AR and/or ER is a contributory factor, provided that the salt or derivative can prevent or inhibit an interaction of a Src family kinase (e.g. Src kinase) with AR or ER. By "derivative", we include the meaning of peptides (e.g. the peptide portion $[(Pro)_n$-$X_r$-His-Pro-His-Ala-Arg-Ile-Lys$]_m$ (SEQ ID NO: 1) is [lys-ile-arg-ala-his-pro-his-$x_r$-$(pro)_n]_m$ (SEQ ID NO: 2) of the molecule above) having one or more residues chemically derivatised by reaction of a functional side group. Such derivatised molecules include, for example, those molecules in which free amino groups have been derivatised to form amine hydrochlorides, p-toluene sulfonyl groups, carbobenzoxy groups, t-butyloxycarbonyl groups, chloroacetyl groups or formyl groups. Free carboxyl groups may be derivatised to form salts, methyl and ethyl esters or other types of esters or hydrazides. Free hydroxyl groups may be derivatised to form O-acyl or O-alkyl derivatives. Also included as derivatives are those peptide portions that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The derivatisation does not include changes in functional groups which change one amino acid to another.

Some useful modifications are designed to increase the stability and, therefore, the half-life of molecules (eg peptides) in solutions, particularly biological fluids, such as blood, plasma or serum, by blocking proteolytic activity in the blood. Thus, a peptide may have a stabilising group at one or both termini. Typical stabilising groups include amido, acetyl, benzyl, phenyl, tosyl, alkoxycarbonyl, alkyl carbonyl, benzyloxycarbonyl and the like end group modifications. Additional modifications include using a “D” amino acid in place of a “L” amino acid at the termini, and amide rather than amino or carboxy termini to inhibit exopeptidase activity. Thus, it is appreciated that the peptide portion $[(Pro)_n\text{-}X_r\text{-His-Pro-His-Ala-Arg-Ile-Lys}]_m$ (SEQ ID NO: 1) is $[\text{lys-ile-arg-ala-his-pro-his-}x_r\text{-}(pro)_n]_m$ (SEQ ID NO: 2) of the molecule defined above may have a capping moiety at one or both ends, preferably a moiety that is less than 200 Da in molecular weight. Further capping moieties include a naftyl group or a polyethylene glycol group. It is appreciated that retro-inverso peptides are already relatively stable and so may not require additional capping moieties.

Accordingly, in a particularly preferred embodiment, the molecule comprises or consists of the structure Ac-Pro-Pro-Pro-His-Pro-His-Ala-Arg-Ile-Lys-$NH_2$(SEQ ID NO: 21) or Ac-Pro-Pro-Thr-His-Pro-His-Ala-Arg-Ile-Lys-$NH_2$(SEQ ID NO: 23), where Ac is an acetyl group.

The molecule of the invention is one that does not reduce or prevent fertility in a subject. As described in the Examples, the inventor has demonstrated that administering the peptide Ac-Pro-Pro-Pro-His-Pro-His-Ala-Arg-Ile-Lys-$NH_2$(SEQ ID NO: 21) to mice does not affect their fertility and it is expected that other molecules that prevent or inhibit an interaction between a Src family kinase (e.g. Src kinase) and AR or ER have the same activity. Methods for assessing fertility in a subject are well known in the art and include assays such as those described in the examples.

In one embodiment, the molecule is administered as a vaccine to generate antibodies. For example, the molecule having the structure defined above may be used in the preparation of an antibody that specifically binds to the AR, and so may be prepared as a vaccine.

It may be desirable to link the molecule to a carrier molecule such as a pro-immunogenic molecule. Suitable examples include bovine serum albumin (BSA) or keyhole limpet hemocyanin (KLH). Additionally or alternatively, the molecule may be comprised in a lipid composition such as a lipid particle, a nanocapsule, a liposome or lipid vesicle. The molecule may also be incorporated in coating capsules for slow release as described further below.

By a condition in which an activity of AR and/or ER is a contributory factor, we include any biological or medical condition or disorder in which at least part of the pathology is mediated by an activity of AR and/or ER. The pathology may be due to an increased or decreased activity of AR and/or ER. The condition may be caused by the AR and/or ER activity or may simply be characterised by AR and/or ER activity. The activity of the AR and/or ER may contribute directly to the condition or may contribute indirectly to the condition. Generally, the condition in which an activity of AR and/or ER is a contributory factor is one where the pathogenesis involves aberrant signalling through the AR and/or ER (e.g. one where cell proliferation is modulated by AR and/or ER). For example, the condition may involve aberrant signalling through the Src family kinase pathway. Such conditions may be diagnosed readily using conventional methods available in the art.

The condition may be non-cancerous (including non-cancerous proliferative disorders) or it may be cancerous (e.g. benign or malignant cancers). The condition may be a reproductive condition, by which we include the meaning of a condition that affects some or all of the organs or tissues of the reproductive system. The reproductive condition may be a gynaecological condition, i.e. one which affects the female reproductive system.

In a first preferred embodiment, the condition is a non-cancerous condition, including any proliferative disorder in which AR and/or ER is a contributory factor. Examples include endometriosis, ovarian cysts, fibroids polyps hyperplasia, neoplasia, anovulatory bleeding, endometrial growth in the scrotum, bladder or prostate, and non-cancerous proliferative conditions in breast tissue. Preferably, the condition is endometriosis.

In a second preferred embodiment, the condition is a cancerous condition and the subject is one who wishes to preserve fertility. By ‘wishes to preserve fertility’ we include the meaning of a subject in whom it is desired not to reduce fertility. For example, the subject may wish to conceive. Such subjects therefore represent a sub-group of cancer patients as, in addition to having cancer, they additionally wish to preserve fertility. Examples of such cancerous conditions include uterine fibroids, fibroids polyps hyperplasia, ovarian cancer, bladder cancer, cervical cancer, uterine cancer, testicular cancer and prostate cancer.

In a third preferred embodiment, the condition (e.g. non-cancerous or cancerous) is a gynaecological condition. Preferably, the condition is endometriosis.

It will be understood that in the first and third preferred embodiments, it may be particularly desirable to use the molecule in subjects that wish to preserve fertility. Thus, in these embodiments also, it is preferred if the subject is one who wishes to preserve fertility. Most preferably, the condition is endometriosis and the subject is one who wishes to preserve fertility.

It is appreciated that the molecule or derivative or fragment thereof described herein may be formulated with a pharmaceutically acceptable excipient, solvent, diluent or carrier (including combinations thereof). The carrier, diluent, solvent or excipient must be “acceptable” in the sense of being compatible with the molecule or derivative and not deleterious to the recipients thereof. Typically, the carriers will be water or saline (e.g. physiological saline) which will be sterile and pyrogen free. Suitable excipients include mannitol and dextrose. Acceptable carriers, solvents, diluents and excipients for therapeutic use are well known in the pharmaceutical art, and are described, for example, in Remington’s Pharmaceutical Sciences, Mack Publishing Co. (A. R. Gennaro ed. 1985). The choice of pharmaceutical carrier, solvent, excipient or diluent can be selected with regard to the intended route of administration and standard pharmaceutical practice. The pharmaceutical compositions may comprise as, or in addition to, the carrier, excipient, solvent or diluent any suitable binder, lubricant, suspending agent, coating agent, or solubilising agent. Preservatives, stabilisers, dyes and even flavouring agents may be provided in the pharmaceutical composition.

The formulations may conveniently be presented in unit dosage form and may be prepared by any of the methods well known in the art of pharmacy. Such methods include the step of bringing into association the molecule with the carrier which constitutes one or more accessory ingredients.

In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured base, usually sucrose and acacia or tragacanth; pastilles comprising the active ingredient in an inert base such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In addition to the ingredients particularly mentioned above, the formulations may include other agents conventional in the art having regard to the type of formulation in question, for example those suitable for oral administration may include flavouring agents.

The molecule or derivative or fragment thereof, or a formulation thereof, may be administered by any conventional method including oral, intranasal, and parenteral (e.g. subcutaneous or intramuscular) injection. Preferred routes include oral, intravenous or subcutaneous injection. The treatment may consist of a single dose or a plurality of doses over a period of time. The molecule or derivative thereof may formulated in a sustained release formulation so as to provide sustained release over a prolonged period of time such as over at least 2 or 4 or 6 or 8 weeks Preferably, the sustained release is provided over at least 4 weeks.

In a particular embodiment, the molecule or derivative or fragment thereof is formulated in a way that allows direct administration to the reproductive system. Thus, the molecule or derivative or fragment thereof may be formulated in a vaginal or rectal suppository, an intravaginal tampon, an intravaginal ring, an intravaginal pessary, an intravaginal sponge, or a medicated intrauterine device (IUD).

It is appreciated that the invention includes a molecule that inhibits or prevents an interaction between a Src family kinase (e.g. Src kinase) and an androgen or estradiol receptor, such as a molecule comprising or consisting of the structure $B_j$-[(Pro)$_n$-$X_r$-His-Pro-His-Ala-Arg-Ile-Lys]$_m$-$R_p$ (SEQ ID NO: 1) or $B_j$-[lys-ile-arg-ala-his-pro-his-$x_r$-(pro)$_n$]$_m$-$R_p$ (SEQ ID NO: 2) defined above, formulated in a way that allows direct administration to the reproductive system or which allows for sustained release. Thus, the invention includes a molecule that inhibits or prevents an interaction between a Src family kinase (e.g. Src kinase) and an androgen or estradiol receptor, such as a molecule comprising or consisting of the structure $B_j$-[(Pro)$_n$-$X_r$-His-Pro-His-Ala-Arg-Ile-Lys]$_m$-$R_p$ (SEQ ID NO: 1) or $B_j$-[lys-ile-arg-ala-his-pro-his-$x_r$-(pro)$_n$]$_m$-$R_p$ (SEQ ID NO: 2) or derivative or fragment thereof, formulated in any of a vaginal or rectal suppository; an intravaginal tampon; an intravaginal ring; an intravaginal pessary; an intravaginal sponge; a medicated intrauterine device (IUD); or a sustained release formulation. In other words, the invention provides a pharmaceutical composition comprising a molecule that inhibits or prevents an interaction between a Src family kinase (e.g. Src kinase) and an androgen or estradiol receptor, which molecule is adapted for formulation in any of a vaginal or rectal suppository; an intravaginal tampon; an intravaginal ring; an intravaginal pessary; an intravaginal sponge; a medicated intrauterine device (IUD); or a sustained release formulation, and which composition optionally comprises a pharmaceutically acceptable excipient, carrier or diluent.

The amount of the molecule or derivative or fragment thereof which is administered to the subject is an amount effective to combat the particular subject's condition. The amount may be determined by the physician.

In an embodiment, the molecule, such as the one comprising or consisting of the structure $B_j$-[(Pro)$_n$-$X_r$-His-Pro-His-Ala-Arg-Ile-Lys]$_m$$R_p$ (SEQ ID NO: 1) or $B_j$-[lys-ile-arg-ala-his-pro-his-$x_r$-(pro)$_n$]$_m$-$R_p$ (SEQ ID NO: 2) defined above, is administered to a subject using a daily dose of between 1-1000 ng, such as a daily dose of 1-900 ng, 1-800 ng, 1-700 ng, 1-600 ng, 1-500 ng, 1-400 ng, 1-300 ng, 1-200 ng or 1-100 ng. Thus, the molecule, such as the one comprising or consisting of the structure $B_j$-[(Pro)$_n$-$X_r$-His-Pro-His-Ala-Arg-Ile-Lys]$_m$-$R_p$ (SEQ ID NO: 1) or $B_j$-[lys-ile-arg-ala-his-pro-his-$x_r$-(pro)$_n$]$_m$-$R_p$ (SEQ ID NO: 2) defined above, may be administered to a subject using a daily dose of at least 1 ng, 10 ng, 20 ng, 30 ng, 40 ng, 50 ng, 60 ng, 70 ng, 80 ng, 90 ng or 100 ng, or at least 150 ng or 200 ng.

In another embodiment, the molecule, such as the one comprising or consisting of the structure $B_j$-[(Pro)$_n$-$X_r$-His-Pro-His-Ala-Arg-Ile-Lys]$_m$$R_p$ (SEQ ID NO: 1) or $B_j$-[lys-ile-arg-ala-his-pro-his-$x_r$-(pro)$_n$]$_m$$R_p$ (SEQ ID NO: 2) defined above, is administered at intervals (e.g. daily, two-daily or weekly) over the course of at least 5, 10, 15, 20, 25, 30, 35, 40, 45, 50, 55 or 60 days, and even over the course of at least 3, 4, 5, 6, 7, 8, 9, 10, 11, 12 or 18 months, or over the course of at least 2, 3, 4 or 5 years. Where the molecule or derivative is administered at intervals, it will be understood that it may be desirable to use different routes of administration at different intervals. For example, the molecule or derivative may be first administered by injection and a follow up dose administered by subcutaneous implant. The optimum administration interval and duration of treatment will generally depend on how severe the condition is.

In one embodiment, the subject is administered a further therapeutic agent in addition to the molecule or derivative described herein. For example, when administering the molecule or derivative thereof to prevent or treat a particular condition, a further therapeutic agent known to be useful for preventing or treating that condition may be administered. Thus, when preventing or treating endometriosis, the further therapeutic agent may be an agent known to prevent or treat endometriosis, when preventing or treating uterine fibroids, the further therapeutic agent may be an agent known to prevent or treat uterine fibroids, and so on.

Typically, the condition in which an activity of AR and/or ER is a contributory factor is a proliferative disorder and so the further therapeutic agent may be any agent that reduces proliferation such as any of a cytostatic agent or a cytosidal agent or an anticancer agent.

It is appreciated that the further therapeutic agent may be administered at the same time as the molecule or derivative thereof described herein (i.e. simultaneous administration optionally in a co-formulation) or at a different time to the molecule or derivative thereof described herein (i.e. sequential administration where the further therapeutic agent is administered before or after the molecule or derivative thereof is administered). The further therapeutic agent may be administered in the same way as the molecule of the invention described herein, or by using the usual administrative routes for that further therapeutic agent.

A second aspect of the invention provides a composition comprising (i) a molecule that inhibits or prevents an interaction between a Src family kinase (e.g. Src kinase) and an androgen or estradiol receptor, and (ii) a therapeutic agent suitable for preventing or treating a non-cancerous condition in which an activity of AR and/or ER is a contributory factor, together with a pharmaceutically acceptable excipient, carrier or diluent. The composition may be a pharmaceutical composition which further comprises a pharmaceutically acceptable excipient, carrier or diluent.

Preferences for the molecule, derivative, the further therapeutic agent, the condition, and the subject to be treated include those mentioned above with respect to the first aspect of the invention. For example, the molecule may comprise or consist of the structure: $B_j$-[$(Pro)_n$-$X_r$-His-Pro-His-Ala-Arg-Ile-Lys]$_m$-$R_p$ (SEQ ID NO: 1), or $B_j$-[lys-ile-arg-ala-his-pro-his-$x_r$-$(pro)_n$]$_m$-$R_p$ (SEQ ID NO: 2), or a derivative or fragment thereof, wherein B is a first chemical moiety, j is 0 or 1, n is an integer from 1-10, m is an integer from 1 to 3, R is a second chemical moiety, p is 0 or 1, and [lys-ile-arg-ala-his-pro-his-$x_r$-$(pro)_n$] (SEQ ID NO: 2) is the retro-inverso peptide of [$(Pro)_n$-$X_r$-His-Pro-His-Ala-Arg-Ile-Lys] (SEQ ID NO: 1). Most preferably, the molecule has the structure Ac-Pro-Pro-Pro-His-Pro-His-Ala-Arg-Ile-Lys-$NH_2$ (SEQ ID NO: 21) or Ac-Pro-Pro-Thr-His-Pro-His-Ala-Arg-Ile-Lys-$NH_2$(SEQ ID NO: 24), where Ac is an acetyl group. Preferably, the subject is a human. Preferably, the further therapeutic agent is one suitable for preventing or treating endometriosis.

Accordingly, the invention includes a composition comprising (i) a molecule that inhibits or prevents an interaction between a Src family kinase (e.g. Src kinase) and an androgen or estradiol receptor, and (ii) a therapeutic agent suitable for preventing or treating a non-cancerous condition in which an activity of AR and/or ER is a contributory factor, together with a pharmaceutically acceptable excipient, carrier or diluent, for use in preventing or treating a non-cancerous condition in which an activity of AR and/or ER is a contributory factor. The composition may be a pharmaceutical composition which further comprises a pharmaceutically acceptable excipient, carrier or diluent.

Similarly, the invention includes the use of a composition comprising (i) a molecule that inhibits or prevents an interaction between a Src family kinase (e.g. Src kinase) and an androgen or estradiol receptor, and (ii) a therapeutic agent suitable for preventing or treating a non-cancerous condition in which an activity of AR and/or ER is a contributory factor, together with a pharmaceutically acceptable excipient, carrier or diluent, in the manufacture of a medicament for preventing or treating a non-cancerous condition in which an activity of AR and/or ER is a contributory factor. The composition may be a pharmaceutical composition which further comprises a pharmaceutically acceptable excipient, carrier or diluent.

It will be appreciated that the invention includes a molecule that inhibits or prevents an interaction between a Src family kinase (e.g. Src kinase) and an androgen or estradiol receptor, for use in preventing or treating a non-cancerous condition in which an activity of AR and/or ER is a contributory factor in a subject, or for use in preventing or treating a cancerous condition in which an activity of AR and/or ER is a contributory factor in a subject who wishes to preserve fertility, or for use in preventing or treating a gynaecological condition in which an activity of AR and/or ER is a contributory factor in a subject, wherein the subject is also administered a therapeutic agent suitable for preventing or treating said condition.

Likewise, it will be understood that the invention includes the use of a molecule that inhibits or prevents an interaction between a Src family kinase (e.g. Src kinase) and an androgen or estradiol receptor, in the manufacture of a medicament for preventing or treating a non-cancerous condition in which an activity of AR and/or ER is a contributory factor in a subject, or for preventing or treating a cancerous condition in which an activity of AR and/or ER is a contributory factor in a subject who wishes to preserve fertility, or for preventing or treating a gynaecological condition in which an activity of AR and/or ER is a contributory factor in a subject, wherein the subject is also administered a therapeutic agent suitable for preventing or treating a non-cancerous condition in which an activity of AR and/or ER is a contributory factor.

Preferably, the molecule may comprise or consist of the structure:

$B_j$-[$(Pro)_n$-$X_r$-His-Pro-His-Ala-Arg-Ile-Lys]$_m$$R_p$ (SEQ ID NO: 1), or $B_j$-[lys-ile-arg-ala-his-pro-his-$x_r$-$(pro)_n$]$_m$-$R_p$ (SEQ ID NO: 2), or a derivative or fragment thereof, wherein B is a first chemical moiety, j is 0 or 1, n is an integer from 1-10, m is an integer from 1 to 3, R is a second chemical moiety, p is 0 or 1, and [lys-ile-arg-ala-his-pro-his-$x_r$-$(pro)_n$] (SEQ ID NO: 2) is the retro-inverso peptide of [$(Pro)_n$-$X_r$-His-Pro-His-Ala-Arg-Ile-Lys] (SEQ ID NO: 1). Most preferably, the molecule has the structure Ac-Pro-Pro-Pro-His-Pro-His-Ala-Arg-Ile-Lys-$NH_2$ (SEQ ID NO: 21) or Ac-Pro-Pro-Thr-His-Pro-His-Ala-Arg-Ile-Lys-$NH_2$(SEQ ID NO: 23), where Ac is an acetyl group.

The inventors have found that molecules that inhibit or prevent an interaction between a Src family kinase and the AR and/or ER may used to prevent or treat a non-cancerous condition in which an activity of AR and/or ER is a contributory factor. Thus, it is appreciated that by assessing the effect of test agents on this interaction, one can identify agents to prevent or treat a non-cancerous condition.

Accordingly, a further aspect of the invention provides a method of selecting an agent to prevent or treat a non-cancerous condition in which an activity of AR and/or ER is a contributory factor, the method comprising determining whether a test agent reduces an interaction between (a) AR or ER or a portion thereof, said portion being capable of binding to a Src family kinase and (b) a Src family kinase or a portion thereof, said portion being capable of binding to AR or ER.

Preferences for AR, ER and Src family kinase, and for the non-cancerous condition include those defined above with respect to the first aspect of the invention.

It will be appreciated that it is not necessary to provide the entire AR or ER, or Src family kinase for the purpose of the screening method. Portions of the AR or ER that are capable of binding to Src family kinase (e.g. Src kinase) may be used, and portions of Src family kinase (e.g. Src kinase) that are capable of binding to the AR or ER may be used. For example, as described above, the SH3 and SH2 domains of Src family kinase (e.g. Src kinase) are believed to mediate the interaction between Src family kinase and each of AR and ER, respectively. Thus, a portion of Src family kinase (e.g. Src kinase) corresponding to the SH3 domain or part thereof capable of binding to AR, or a portion of Src family kinase (e.g. Src kinase) corresponding to the SH2 domain or part thereof capable of binding to ER, may be used. Likewise, a portion of the AR corresponding to amino acid residues 377-386 of AR, believed to mediate the interaction between AR and the SH3 domain of Src family kinase (e.g. Src kinase), may be used. Other suitable portions may be determined by one of skilled in the art and are described, for example, in Migliaccio et al (Oncogene 2007, 26: 6619) and Migliaccio et al (Cancer Research 2005, 65(22):10585-93).

The test agent may be any suitable test agent including a polypeptide, an antibody, a small molecule, a natural product, a peptidomimetic or a nucleic acid. It is appreciated that a library of test agents may be screened as part of a high throughput screen.

Various techniques can be used to determine a test agent's effect on the interaction between AR or ER and Src family kinase (e.g. Src kinase) or portions thereof, for example as described above and which are well known in the art (e.g. from Migliaccio et al (Oncogene 2007, 26: 6619) and Migliaccio et al (Cancer Research 2005, 65(22):10585-93).

In one embodiment, the method comprises the step of isolating a test agent that reduces an interaction between (a) AR or ER or a portion thereof, said portion being capable of binding to a Src family kinase and (b) a Src family kinase or a portion thereof, said portion being capable of binding to AR or ER.

Preferably, the test agent selected is one that reduces an interaction (a) AR or ER or a portion thereof, said portion being capable of binding to a Src family kinase and (b) a Src family kinase or a portion thereof, said portion being capable of binding to AR or ER, by a factor of at least 10%, 20%, 30%, 40% or 50% of the original binding in the absence of the test agent, and more preferably by a factor of at least 60%, 70%, 80%, 90% or 95%.

In one embodiment, the method further comprises identifying the test agent as an agent which prevents or treats a non-cancerous condition in which an activity of AR and/or ER is a contributory factor. For example, the method may further comprise assessing the efficacy of the test agent in an appropriate assay for the particular condition in question (e.g. an animal model of the condition). For instance, the method may be used to select an agent to prevent or treat endometriosis such that it involves assessing the effect of the agent in a model of endometriosis. Suitable models of such conditions are well known in the art.

It will be appreciated that the test agent selected is an agent that inhibits or prevents an interaction between a Src family kinase and an AR or ER within the meaning of the first aspect of the invention and so can be used as such.

It is appreciated that in the method described herein, which may be drug screening methods, a term well known to those skilled in the art, the test agent may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes or the blood:brain barrier, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

In one embodiment, the method is performed in vitro. By in vitro we include both cell-free assays and cell-based assays. For example, the method may be performed in isolated human cell lines or in cell lines that can be easily manipulated within a laboratory (e.g. *Escherichia coli* and *Saccharomyces cerevisiae*).

In an alternative embodiment, the method is performed in vivo, for example in animal models of the particular conditions (e.g. endometriosis).

The invention provides any molecule, use, method or composition substantially as described herein.

The invention will now be described with the aid of the following figures and examples.

FIG. 1: Mouse weight (g) in dose ranging study.

Figure 2:
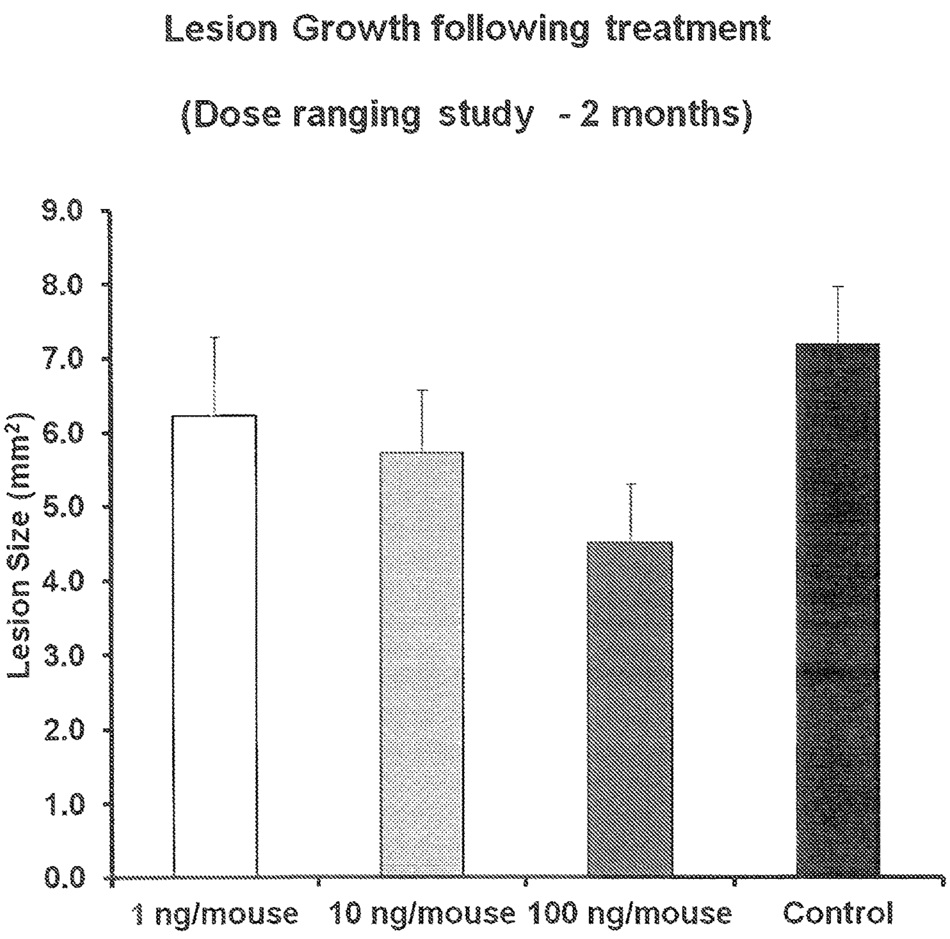

FIG. 2: Lesion growth following treatment (mm2) in dose ranging study.

FIG. 3: Homologues of PPPHPHARIK (SEQ ID NO: 21) in a selection of species.

EXAMPLE 1: THE PEPTIDE AC-PPPHPHARIK-NH2 (SEQ ID NO: 21) EXHIBITS THERAPEUTIC EFFICACY AGAINST ENDOMETRIOSIS WITHOUT AFFECTING FERTILITY

Summary

Two studies have been carried out which demonstrate the efficacy of the peptide Ac-PPPHPHARIK-NH2 (SEQ ID NO: 21) (also defined in Tables 1-4 as ValiRx1) in treating endometriosis without reducing fertility.

Results

In a first study, a total of 4 treatment and 5 control animals were generated in a novel in-vivo model of endometriosis (Research Horizons, University of Cambridge, 2009 Issue 8, GB 0715635.9) K-rasV12/Ah-Cre transgenic mice were crossed with Rosa26R mice to generate KrasV12+/−/Ah-Cre+/−/ROSA26R-LacZ+/− transgenic mice. The F1 offspring were inbred to generate F2 K-rasV12+/−/Ah-Cre+/+/ROSA26R-LacZ+/+ transgenic mice. The presence of the transgenes was determined by PCR using gene specific primers for K-ras, Cre and Rosa26R-LacZ. Tissue was collected from donor animals previously treated with hormones etc. and was divided between wild-type animals that were then injected with drug or vehicle for 21 days.

From a total of four treated animals, three showed complete absence of lesion following treatment with one non-responder. In the control groups totaling 5 animals, one failed to develop a lesion.

A second study was designed to evaluate the effect of the peptide on reproduction in healthy mice and efficacy against autografted lesions derived from one uteri re-implanted in the same animal (Becker et al, AM J Pathol 178 (4): 1782-91).

Estrous Cycling 8-10 week old, female nulliparous C57BL6 mice were acclimatised for 1 week. A group of 10 animals were treated with 10 ng of peptide injected subcutaneously 3 days prior to experimentation with a group of 10 controls dosed with vehicle alone. Daily vaginal smears were taken for a period of 10 days. Normal smears were obtained in all cases Mating (Female Treatment Group)

8-10 week old, female nulliparous C57BL6 mice were acclimatised for 1 week. A group of 10 female animals were dosed with 10 ng of peptide injected subcutaneously 3 days prior to experimentation with a control group of 10 animals treated with vehicle alone.

5 male C57BL6 animals were introduced and the females checked daily for mucous plug (before 9 a.m.). When mucous plug was recorded the females were evaluated for:

a) Length of possible pregnancy (days)

b) Number of offspring c) Anomalies in offspring

All animals delivered normal litters (with the exception of one of the dosed group)

Mating (Male Treatment Group)

8-10 week old, nulliparous C57BL6 mice were acclimatised for 1 week. A group of 5 male animals were dosed with 10 ng of peptide injected subcutaneously 3 days prior to experimentation with a control group of 5 animals dosed with vehicle alone (10 ng daily SC). 10 non-treated female C57BL6 animals were introduced to each group and the females checked daily for mucous plug (before 9 a.m.). When mucous plug was recorded the females were evaluated for:

a) Length of possible pregnancy (days)

b) Number of offspring c) Anomalies in offspring

As above all animals delivered normal litters

Mating (2 Generation from Treated Females)

Offspring from dosed females were mated and checked for fertility to determine possible inheritable effects. Animals were evaluated as above following plugging with no abnormalities noted.

Dose Ranging Prevention Study 8-10 week old, female nulliparous C57BL6 mice were each transplanted with 6× plugs of uterine tissue from donor animals after one week of acclimatisation. Three groups of 5 animals began immediate daily dosing with 1 ng, 10 ng or 100 ng of peptide injected subcutaneously with the ARP peptide and a control group of 5 animals treated with vehicle alone. Lesion growth following treatment in the dosed group was significantly reduced compared to the control group (see FIG. 2).

The model resulted in excellent lesion establishment (97.67%-100%, Table 4). A reduction in lesion burden (6.02 $mm^2$, 5.53 $mm^2$ and 4.52 $mm^2$ vs. 7.18 $mm^2$, Table 2) and growth (6.23 $mm^2$, 5.72 $mm^2$ and 4.52 vs 7.18 $mm^2$ Table 3).

With regard to dose, there is an option to synchronize estrous cycle by single injection of estrogen 2-3 days prior to surgery.

The data obtained from the experiments described above are illustrated in FIGS. 1 and 2 and Tables 1-4.

TABLE 1

Mouse weight following treatment with Valirx1 or control without treatment

| Mouse # | Treatment | Approach | Application | Dose | Frequency | Weight | Average Weight | STD | SEM |
|---|---|---|---|---|---|---|---|---|---|
| 1 | ValiRx1 | Prevention | s.c. injection | 1 ng/mouse | Daily | 25 | | | |
| 2 | ValiRx1 | Prevention | s.c. injection | 1 ng/mouse | Daily | 27 | | | |
| 3 | ValiRx1 | Prevention | s.c. injection | 1 ng/mouse | Daily | 23 | | | |
| 4 | ValiRx1 | Prevention | s.c. injection | 1 ng/mouse | Daily | 27 | | | |
| 5 | ValiRx1 | Prevention | s.c. injection | 1 ng/mouse | Daily | 24 | 25.2 | 1.79 | 0.8 |
| 1 | ValiRx1 | Prevention | s.c. injection | 10 ng/mouse | Daily | 30 | | | |
| 2 | ValiRx1 | Prevention | s.c. injection | 10 ng/mouse | Daily | 30 | | | |
| 3 | ValiRx1 | Prevention | s.c. injection | 10 ng/mouse | Daily | 23 | | | |
| 4 | ValiRx1 | Prevention | s.c. injection | 10 ng/mouse | Daily | 30 | | | |
| 5 | ValiRx1 | Prevention | s.c. injection | 10 ng/mouse | Daily | 24 | 27.4 | 3.58 | 1.6 |
| 1 | ValiRx1 | Prevention | s.c. injection | 100 ng/mouse | Daily | 25 | | | |
| 2 | ValiRx1 | Prevention | s.c. injection | 100 ng/mouse | Daily | 27 | | | |
| 3 | ValiRx1 | Prevention | s.c. injection | 100 ng/mouse | Daily | 22 | | | |
| 4 | ValiRx1 | Prevention | s.c. injection | 100 ng/mouse | Daily | 34 | | | |
| 5 | ValiRx1 | Prevention | s.c. injection | 100 ng/mouse | Daily | 34 | 28.4 | 5.41 | 2.4207 |
| 1 | Control | Prevention | s.c. injection | n/a | Daily | 28 | | | |
| 2 | Control | Prevention | s.c. injection | n/a | Daily | 27 | | | |
| 3 | Control | Prevention | s.c. injection | n/a | Daily | 30 | | | |
| 4 | Control | Prevention | s.c. injection | n/a | Daily | 25 | | | |
| 5 | Control | Prevention | s.c. injection | n/a | Daily | 28 | 27.6 | 1.82 | 0.8124 |

TABLE 2

Lesion Burden following treatment with various doses of Valirx1 or control without treatment

| | | BURDEN | | | | P1 | P2 | P3 | P4 | P5 | P6 | Ave | Mean | StDev | SEM | Ttest | | |
|---|---|---|---|---|---|---|---|---|---|---|---|---|---|---|---|---|---|---|
| 1 | ValiRx1 | Prevention | s.c. injection | 1 ng/mouse | Daily | 15.1 | 5.7 | 8.0 | 3.8 | 0.2 | 6.2 | 6.5 | | | | | | |
| 2 | ValiRx1 | Prevention | s.c. injection | 1 ng/mouse | Daily | 10.2 | 10.6 | 16.6 | 3.8 | 0.5 | 9.4 | 8.5 | | | | | | |
| 3 | ValiRx1 | Prevention | s.c. injection | 1 ng/mouse | Daily | 1.8 | 0.2 | 0.1 | 0.0 | 3.5 | 1.1 | 1.1 | | | | | | |
| 4 | ValiRx1 | Prevention | s.c. injection | 1 ng/mouse | Daily | 1.1 | 3.1 | 2.5 | 0.2 | 1.1 | 3.5 | 1.9 | | | | | | |
| 5 | ValiRx1 | Prevention | s.c. injection | 1 ng/mouse | Daily | 4.2 | 16.7 | 15.2 | 17.0 | 11.2 | 8.0 | 12.1 | 6.02 | 5.69 | 1.04 | | | |
| 1 | ValiRx1 | Prevention | s.c. injection | 10 ng/mouse | Daily | 1.0 | 3.5 | 10.9 | 1.0 | 1.0 | 0.2 | 2.9 | | | | | | |
| 2 | ValiRx1 | Prevention | s.c. injection | 10 ng/mouse | Daily | 7.3 | 10.0 | 4.5 | 6.7 | 7.1 | 4.5 | 6.7 | | | | | | |
| 3 | ValiRx1 | Prevention | s.c. injection | 10 ng/mouse | Daily | 12.6 | 7.0 | 9.6 | 5.4 | 21.1 | 12.1 | 11.3 | | | | | | |
| 4 | ValiRx1 | Prevention | s.c. injection | 10 ng/mouse | Daily | 3.1 | 3.5 | 3.5 | 3.0 | 3.5 | 3.1 | 3.3 | | | | | | |
| 5 | ValiRx1 | Prevention | s.c. injection | 10 ng/mouse | Daily | 1.1 | 2.5 | 3.5 | 0.0 | 4.0 | 9.7 | 3.5 | 5.53 | 4.63 | 0.85 | | | |
| 1 | ValiRx1 | Prevention | s.c. injection | 100 ng/mouse | Daily | 7.0 | 18.5 | 11.0 | 8.4 | 12.6 | 13.2 | 11.8 | | | | | | |
| 2 | ValiRx1 | Prevention | s.c. injection | 100 ng/mouse | Daily | 4.5 | 2.8 | 2.3 | 0.2 | 1.0 | 0.3 | 1.8 | | | | | | |
| 3 | ValiRx1 | Prevention | s.c. injection | 100 ng/mouse | Daily | 2.8 | 2.3 | 2.3 | 3.8 | 7.5 | 0.3 | 3.2 | | | | | | |
| 4 | ValiRx1 | Prevention | s.c. injection | 100 ng/mouse | Daily | 2.0 | 3.1 | 3.5 | 2.5 | 3.8 | 2.8 | 3.0 | | | | | | |
| 5 | ValiRx1 | Prevention | s.c. injection | 100 ng/mouse | Daily | 1.5 | 3.5 | 4.9 | 1.8 | 2.0 | 3.5 | 2.9 | 4.52 | 4.31 | 0.79 | | | |
| 1 | Control | Prevention | s.c. injection | n/a | Daily | 0.2 | 4.9 | 6.6 | 9.3 | 9.6 | 10.2 | 6.8 | | | | | | |
| 2 | Control | Prevention | s.c. injection | n/a | Daily | 7.5 | 6.6 | 9.1 | 7.1 | 9.8 | 7.5 | 7.9 | | | | | | |
| 3 | Control | Prevention | s.c. injection | n/a | Daily | 2.5 | 3.8 | 3.8 | 7.0 | 6.2 | 1.8 | 4.2 | | | | | | |
| 4 | Control | Prevention | s.c. injection | n/a | Daily | 4.2 | 4.9 | 5.3 | 9.6 | 8.5 | 4.9 | 6.2 | | | | | | |
| 5 | Control | Prevention | s.c. injection | n/a | Daily | 7.0 | 15.7 | 16.7 | 0.5 | 18.4 | 6.2 | 10.8 | 7.18 | 4.26 | 0.78 | 0.37 | 0.15 | 0.01908652 |

TABLE 3

Lesion Growth following treatment with various doses of Valirx1 or control without treatment

| | | Growth | | | | P1 | P2 | P3 |
|---|---|---|---|---|---|---|---|---|
| 1 | ValiRx1 | Prevention | s.c. injection | 1 ng/mouse | Daily | 15.1 | 5.694 | 8.042 |
| 2 | ValiRx1 | Prevention | s.c. injection | 1 ng/mouse | Daily | 10.18 | 10.56 | 16.62 |
| 3 | ValiRx1 | Prevention | s.c. injection | 1 ng/mouse | Daily | 1.767 | 0.196 | 0.126 |

TABLE 3-continued

Lesion Growth following treatment with various doses of Valirx1 or control without treatment

| | | | | | | | | |
|---|---|---|---|---|---|---|---|---|
| 4 | ValiRx1 | Prevention | s.c. injection | 1 ng/mouse | Daily | 1.131 | 3.142 | 2.545 |
| 5 | ValiRx1 | Prevention | s.c. injection | 1 ng/mouse | Daily | 4.155 | 16.74 | 15.21 |
| 1 | ValiRx1 | Prevention | s.c. injection | 10 ng/mouse | Daily | 0.95 | 3.464 | 10.95 |
| 2 | ValiRx1 | Prevention | s.c. injection | 10 ng/mouse | Daily | 7.288 | 10.02 | 4.524 |
| 3 | ValiRx1 | Prevention | s.c. injection | 10 ng/mouse | Daily | 12.57 | 7.037 | 9.621 |
| 4 | ValiRx1 | Prevention | s.c. injection | 10 ng/mouse | Daily | 3.142 | 3.464 | 3.464 |
| 5 | ValiRx1 | Prevention | s.c. injection | 10 ng/mouse | Daily | 1.131 | 2.545 | 3.464 |
| 1 | ValiRx1 | Prevention | s.c. injection | 100 ng/mouse | Daily | 7.037 | 18.47 | 11 |
| 2 | ValiRx1 | Prevention | s.c. injection | 100 ng/mouse | Daily | 4.453 | 2.827 | 2.27 |
| 3 | ValiRx1 | Prevention | s.c. injection | 100 ng/mouse | Daily | 2.827 | 2.27 | 2.27 |
| 4 | ValiRx1 | Prevention | s.c. injection | 100 ng/mouse | Daily | 2.011 | 3.142 | 3.464 |
| 5 | ValiRx1 | Prevention | s.c. injection | 100 ng/mouse | Daily | 1.539 | 3.464 | 4.909 |
| 1 | Control | Prevention | s.c. injection | n/a | Daily | 0.196 | 4.909 | 6.605 |
| 2 | Control | Prevention | s.c. injection | n/a | Daily | 7.548 | 6.605 | 9.079 |
| 3 | Control | Prevention | s.c. injection | n/a | Daily | 2.545 | 3.801 | 3.801 |
| 4 | Control | Prevention | s.c. injection | n/a | Daily | 4.155 | 4.909 | 5.309 |
| 5 | Control | Prevention | s.c. injection | n/a | Daily | 7.037 | 15.71 | 16.74 |

| | P4 | M1 | M2 | Ave | Mean | StDev | SEM | Ttest | |
|---|---|---|---|---|---|---|---|---|---|
| 1 | 3.801 | 0.196 | 6.158 | 6.5 | | | | | |
| 2 | 3.801 | 0.503 | 9.425 | 8.5 | | | | | |
| 3 | | 3.456 | 1.131 | 1.3 | | | | | |
| 4 | 0.196 | 1.131 | 3.464 | 1.9 | | | | | |
| 5 | 16.96 | 11.2 | 8.042 | 12.1 | 6.23 | 5.67 | 1.05 | | |
| 1 | 0.95 | 0.95 | 0.196 | 2.9 | | | | | |
| 2 | 6.739 | 7.069 | 4.524 | 6.7 | | | | | |
| 3 | 5.372 | 21.11 | 12.06 | 11.3 | | | | | |
| 4 | 2.969 | 3.464 | 3.142 | 3.3 | | | | | |
| 5 | | 3.958 | 9.66 | 4.2 | 5.72 | 4.59 | 0.85 | | |
| 1 | 8.357 | 12.57 | 13.2 | 11.8 | | | | | |
| 2 | 0.196 | 0.95 | 0.283 | 1.8 | | | | | |
| 3 | 3.801 | 7.548 | 0.283 | 3.2 | | | | | |
| 4 | 2.545 | 3.801 | 2.835 | 3.0 | | | | | |
| 5 | 1.767 | 2.011 | 3.464 | 2.9 | 4.52 | 4.31 | 0.79 | | |
| 1 | 9.346 | 9.621 | 10.18 | 6.8 | | | | | |
| 2 | 7.061 | 9.802 | 7.548 | 7.9 | | | | | |
| 3 | 7.037 | 6.158 | 1.767 | 4.2 | | | | | |
| 4 | 9.55 | 8.545 | 4.909 | 6.2 | | | | | |
| 5 | 0.503 | 18.38 | 6.158 | 10.8 | 7.18 | 4.26 | 0.78 | 0.47 | 0.019086519 |

TABLE 4

Lesion establishment

| ESTABLISHMENT | | | | | | P1 | P2 | P3 | P4 | M1 | M2 | Ave | Mean | StDev | SEM | Ttest |
|---|---|---|---|---|---|---|---|---|---|---|---|---|---|---|---|---|
| 1 | ValiRx1 | Prevention | s.c. injection | 1 ng/mouse | Daily | 1 | 1 | 1 | 1 | 1 | 1 | 100 | | | | |
| 2 | ValiRx1 | Prevention | s.c. injection | 1 ng/mouse | Daily | 1 | 1 | 1 | 1 | 1 | 1 | 100 | | | | |
| 3 | ValiRx1 | Prevention | s.c. injection | 1 ng/mouse | Daily | 1 | 1 | 1 | 0 | 1 | 1 | 83.33 | | | | |
| 4 | ValiRx1 | Prevention | s.c. injection | 1 ng/mouse | Daily | 1 | 1 | 1 | 1 | 1 | 1 | 100 | | | | |
| 5 | ValiRx1 | Prevention | s.c. injection | 1 ng/mouse | Daily | 1 | 1 | 1 | 1 | 1 | 1 | 100 | 96.67 | 7.45 | 1.36 | |
| 1 | ValiRx1 | Prevention | s.c. injection | 10 ng/mouse | Daily | 1 | 1 | 1 | 1 | 1 | 1 | 100 | | | | |
| 2 | ValiRx1 | Prevention | s.c. injection | 10 ng/mouse | Daily | 1 | 1 | 1 | 1 | 1 | 1 | 100 | | | | |
| 3 | ValiRx1 | Prevention | s.c. injection | 10 ng/mouse | Daily | 1 | 1 | 1 | 1 | 1 | 1 | 100 | | | | |
| 4 | ValiRx1 | Prevention | s.c. injection | 10 ng/mouse | Daily | 1 | 1 | 1 | 1 | 1 | 1 | 100 | | | | |
| 5 | ValiRx1 | Prevention | s.c. injection | 10 ng/mouse | Daily | 1 | 1 | 1 | 0 | 1 | 1 | 83.33 | 96.67 | 7.45 | 1.36 | |
| 1 | ValiRx1 | Prevention | s.c. injection | 100 ng/mouse | Daily | 1 | 1 | 1 | 1 | 1 | 1 | 100 | | | | |
| 2 | ValiRx1 | Prevention | s.c. injection | 100 ng/mouse | Daily | 1 | 1 | 1 | 1 | 1 | 1 | 100 | | | | |
| 3 | ValiRx1 | Prevention | s.c. injection | 100 ng/mouse | Daily | 1 | 1 | 1 | 1 | 1 | 1 | 100 | | | | |
| 4 | ValiRx1 | Prevention | s.c. injection | 100 ng/mouse | Daily | 1 | 1 | 1 | 1 | 1 | 1 | 100 | | | | |
| 5 | ValiRx1 | Prevention | s.c. injection | 100 ng/mouse | Daily | 1 | 1 | 1 | 1 | 1 | 1 | 100 | 100.00 | 0.00 | 0.00 | |
| 1 | Control | Prevention | s.c. injection | n/a | Daily | 1 | 1 | 1 | 1 | 1 | 1 | 100 | | | | |
| 2 | Control | Prevention | s.c. injection | n/a | Daily | 1 | 1 | 1 | 1 | 1 | 1 | 100 | | | | |
| 3 | Control | Prevention | s.c. injection | n/a | Daily | 1 | 1 | 1 | 1 | 1 | 1 | 100 | | | | |
| 4 | Control | Prevention | s.c. injection | n/a | Daily | 1 | 1 | 1 | 1 | 1 | 1 | 100 | | | | |
| 5 | Control | Prevention | s.c. injection | n/a | Daily | 1 | 1 | 1 | 1 | 1 | 1 | 100 | 100.00 | 0.00 | 0.00 | |

The invention claimed is:

1. A method of treating endometriosis in a subject in which it is desired to preserve fertility, in which an interaction between a Src family kinase and an androgen receptor (AR) and/or estradiol receptor (ER) is a contributory factor to endometriosis, the method comprising, administering to the subject an effective amount of a molecule that inhibits an interaction between the Src family kinase and the AR and/or the ER, wherein the molecule comprises the structure:

Bj-Pro-Pro-Pro-His-Pro-His-Ala-Arg-Ile-Lys-Rp (SEQ ID NO: 21), wherein B is a first chemical moiety that is an acetyl group, j is 0 or 1, R is a second chemical moiety that is an NH2 group, and p is 0 or 1, wherein said inhibition occurs without a contraceptive effect in the subject.

* * * * *

SEQUENCE LISTING

<160> NUMBER OF SEQ ID NOS: 70

<210> SEQ ID NO 1
<211> LENGTH: 9
<212> TYPE: PRT
<213> ORGANISM: Artificial Sequence
<220> FEATURE:
<223> OTHER INFORMATION: Preferred embodiment
<220> FEATURE:
<221> NAME/KEY: REPEAT
<222> LOCATION: 1
<223> OTHER INFORMATION: Wherein this feature may be between 1 and 10.
<220> FEATURE:
<221> NAME/KEY: VARIANT
<222> LOCATION: 2
<223> OTHER INFORMATION: Wherein this feature could be any naturally occurring amino acid.
<220> FEATURE:
<221> NAME/KEY: REPEAT
<222> LOCATION: 2
<223> OTHER INFORMATION: Wherein this feature may be between 0 and 2.
<220> FEATURE:
<221> NAME/KEY: REPEAT
<222> LOCATION: 1 - 9
<223> OTHER INFORMATION: Wherein this feature may be between 1 and 3.

<400> SEQUENCE: 1

Pro Xaa His Pro His Ala Arg Ile Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Preferred embodiment - retro inverso
<220> FEATURE:
<221> NAME/KEY: VARIANT
<222> LOCATION: 8
<223> OTHER INFORMATION: Wherein this feature could be any naturally occurring amino acid.
<220> FEATURE:
<221> NAME/KEY: REPEAT
<222> LOCATION: 8
<223> OTHER INFORMATION: Wherein this feature may be between 0 and 2.
<220> FEATURE:
<221> NAME/KEY: REPEAT
<222> LOCATION: 9
<223> OTHER INFORMATION: Wherein this feature may be between 1 and 10.
<220> FEATURE:
<221> NAME/KEY: REPEAT
<222> LOCATION: 1 - 9
<223> OTHER INFORMATION: Wherein this feature may be between 1 and 3.
<220> FEATURE:
<221> NAME/KEY: MISC_FEATURE
<222> LOCATION: 1 - 9
<223> OTHER INFORMATION: Wherein these amino acids are D-amino acids.

<400> SEQUENCE: 2

Lys Ile Arg Ala His Pro His Xaa Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Example of suitable fragment

<400> SEQUENCE: 3

His Pro His Ala Arg Ile Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Example of suitable fragment

<400> SEQUENCE: 4

His Pro His Ala Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Example of suitable fragment

<400> SEQUENCE: 5

Pro His Pro His Ala Arg
1               5

<210> SEQ ID NO 6
<211> LENGTH: 4
<212> TYPE: PRT
<213> ORGANISM: Artificial Sequence
<220> FEATURE:
<223> OTHER INFORMATION: Example of suitable fragment

<400> SEQUENCE: 6

Pro His Pro His
1

<210> SEQ ID NO 7
<211> LENGTH: 5
<212> TYPE: PRT
<213> ORGANISM: Artificial Sequence
<220> FEATURE:
<223> OTHER INFORMATION: Example of suitable fragment

<400> SEQUENCE: 7

Pro Pro His Pro His
1               5

<210> SEQ ID NO 8
<211> LENGTH: 6
<212> TYPE: PRT
<213> ORGANISM: Artificial Sequence
<220> FEATURE:
<223> OTHER INFORMATION: Example of suitable fragment

<400> SEQUENCE: 8

Pro Pro Pro His Pro His
1               5

<210> SEQ ID NO 9
<211> LENGTH: 4
<212> TYPE: PRT
<213> ORGANISM: Artificial Sequence
<220> FEATURE:
<223> OTHER INFORMATION: Example of suitable fragment

<400> SEQUENCE: 9

Pro Pro His Pro
1

-continued

```
<210> SEQ ID NO 10
<211> LENGTH: 5
<212> TYPE: PRT
<213> ORGANISM: Artificial Sequence
<220> FEATURE:
<223> OTHER INFORMATION: Example of suitable fragment

<400> SEQUENCE: 10

Pro Pro Pro His Pro
1               5


<210> SEQ ID NO 11
<211> LENGTH: 4
<212> TYPE: PRT
<213> ORGANISM: Artificial Sequence
<220> FEATURE:
<223> OTHER INFORMATION: Example of suitable fragment

<400> SEQUENCE: 11

Pro Pro Pro His
1


<210> SEQ ID NO 12
<211> LENGTH: 7
<212> TYPE: PRT
<213> ORGANISM: Artificial Sequence
<220> FEATURE:
<223> OTHER INFORMATION: Acetylated example of suitable fragment

<400> SEQUENCE: 12

His Pro His Ala Arg Ile Lys
1               5


<210> SEQ ID NO 13
<211> LENGTH: 5
<212> TYPE: PRT
<213> ORGANISM: Artificial Sequence
<220> FEATURE:
<223> OTHER INFORMATION: Acetylated example of suitable fragment

<400> SEQUENCE: 13

His Pro His Ala Arg
1               5


<210> SEQ ID NO 14
<211> LENGTH: 6
<212> TYPE: PRT
<213> ORGANISM: Artificial Sequence
<220> FEATURE:
<223> OTHER INFORMATION: Acetylated example of suitable fragment

<400> SEQUENCE: 14

Pro His Pro His Ala Arg
1               5


<210> SEQ ID NO 15
<211> LENGTH: 4
<212> TYPE: PRT
<213> ORGANISM: Artificial Sequence
<220> FEATURE:
<223> OTHER INFORMATION: Acetylated example of suitable fragment

<400> SEQUENCE: 15

Pro His Pro His
1


<210> SEQ ID NO 16
```

-continued

<211> LENGTH: 5
<212> TYPE: PRT
<213> ORGANISM: Artificial Sequence
<220> FEATURE:
<223> OTHER INFORMATION: Acetylated example of suitable fragment

<400> SEQUENCE: 16

Pro Pro His Pro His
1 5

<210> SEQ ID NO 17
<211> LENGTH: 6
<212> TYPE: PRT
<213> ORGANISM: Artificial Sequence
<220> FEATURE:
<223> OTHER INFORMATION: Acetylated example of suitable fragment

<400> SEQUENCE: 17

Pro Pro Pro His Pro His
1 5

<210> SEQ ID NO 18
<211> LENGTH: 4
<212> TYPE: PRT
<213> ORGANISM: Artificial Sequence
<220> FEATURE:
<223> OTHER INFORMATION: Acetylated example of suitable fragment

<400> SEQUENCE: 18

Pro Pro His Pro
1

<210> SEQ ID NO 19
<211> LENGTH: 5
<212> TYPE: PRT
<213> ORGANISM: Artificial Sequence
<220> FEATURE:
<223> OTHER INFORMATION: Acetylated example of suitable fragment

<400> SEQUENCE: 19

Pro Pro Pro His Pro
1 5

<210> SEQ ID NO 20
<211> LENGTH: 4
<212> TYPE: PRT
<213> ORGANISM: Artificial Sequence
<220> FEATURE:
<223> OTHER INFORMATION: Acetylated example of suitable fragment

<400> SEQUENCE: 20

Pro Pro Pro His
1

<210> SEQ ID NO 21
<211> LENGTH: 10
<212> TYPE: PRT
<213> ORGANISM: Homo sapiens

<400> SEQUENCE: 21

Pro Pro Pro His Pro His Ala Arg Ile Lys
1 5 10

<210> SEQ ID NO 22
<211> LENGTH: 10
<212> TYPE: PRT
<213> ORGANISM: Artificial Sequence -continued
<220> FEATURE:
<223> OTHER INFORMATION: Retro-inverso peptide of Homo sapiens AR.
<220> FEATURE:
<221> NAME/KEY: MISC_FEATURE
<222> LOCATION: 1 - 10
<223> OTHER INFORMATION: Wherein these amino acids are D-amino acids.

<400> SEQUENCE: 22

Lys Ile Arg Ala His Pro His Pro Pro Pro
1 5 10

<210> SEQ ID NO 23
<211> LENGTH: 10
<212> TYPE: PRT
<213> ORGANISM: Mus musculus

<400> SEQUENCE: 23

Pro Pro Thr His Pro His Ala Arg Ile Lys
1 5 10

<210> SEQ ID NO 24
<211> LENGTH: 10
<212> TYPE: PRT
<213> ORGANISM: Artificial Sequence
<220> FEATURE:
<223> OTHER INFORMATION: Retro-inverso peptide of Mus musculus AR.
<220> FEATURE:
<221> NAME/KEY: MISC_FEATURE
<222> LOCATION: 1 - 10
<223> OTHER INFORMATION: Wherein these amino acids are D-amino acids.

<400> SEQUENCE: 24

Lys Ile Arg Ala His Pro His Thr Pro Pro
1 5 10

<210> SEQ ID NO 25
<211> LENGTH: 10
<212> TYPE: PRT
<213> ORGANISM: Rattus rattus

<400> SEQUENCE: 25

Pro Pro Thr His Pro His Ala Arg Ile Lys
1 5 10

<210> SEQ ID NO 26
<211> LENGTH: 10
<212> TYPE: PRT
<213> ORGANISM: Artificial Sequence
<220> FEATURE:
<223> OTHER INFORMATION: Retro-inverso peptide of Rattus rattus AR.
<220> FEATURE:
<221> NAME/KEY: MISC_FEATURE
<222> LOCATION: 1 - 10
<223> OTHER INFORMATION: Wherein these amino acids are D-amino acids.

<400> SEQUENCE: 26

Lys Ile Arg Ala His Pro His Thr Pro Pro
1 5 10

<210> SEQ ID NO 27
<211> LENGTH: 10
<212> TYPE: PRT
<213> ORGANISM: Sus scrofa

<400> SEQUENCE: 27

Pro Pro Pro His Pro His Ala Arg Ile Lys
1 5 10

<210> SEQ ID NO 28
<211> LENGTH: 10
<212> TYPE: PRT
<213> ORGANISM: Papio hamadryas

<400> SEQUENCE: 28

```
Pro Pro Pro His Pro His Ala Arg Ile Lys
1               5                   10
```

<210> SEQ ID NO 29
<211> LENGTH: 10
<212> TYPE: PRT
<213> ORGANISM: Pan troglodytes

<400> SEQUENCE: 29

```
Pro Pro Pro His Pro His Ala Arg Ile Lys
1               5                   10
```

<210> SEQ ID NO 30
<211> LENGTH: 10
<212> TYPE: PRT
<213> ORGANISM: Macaca mulatta

<400> SEQUENCE: 30

```
Pro Pro Pro His Pro His Ala Arg Ile Lys
1               5                   10
```

<210> SEQ ID NO 31
<211> LENGTH: 10
<212> TYPE: PRT
<213> ORGANISM: Cynomolgus monkey

<400> SEQUENCE: 31

```
Pro Pro Pro His Pro His Ala Arg Ile Lys
1               5                   10
```

<210> SEQ ID NO 32
<211> LENGTH: 10
<212> TYPE: PRT
<213> ORGANISM: Red squirrel

<400> SEQUENCE: 32

```
Pro Pro Pro His Pro His Ala Arg Ile Lys
1               5                   10
```

<210> SEQ ID NO 33
<211> LENGTH: 10
<212> TYPE: PRT
<213> ORGANISM: Felis catus

<400> SEQUENCE: 33

```
Pro Pro Pro His Pro His Ala Arg Ile Lys
1               5                   10
```

<210> SEQ ID NO 34
<211> LENGTH: 10
<212> TYPE: PRT
<213> ORGANISM: Galidia elegans

<400> SEQUENCE: 34

```
Pro Pro Pro His Pro His Ala Arg Ile Lys
1               5                   10
```

<210> SEQ ID NO 35

-continued

<211> LENGTH: 10
<212> TYPE: PRT
<213> ORGANISM: Eupleres goudotii

<400> SEQUENCE: 35

Pro Pro Pro His Pro His Ala Arg Ile Lys
1 5 10

<210> SEQ ID NO 36
<211> LENGTH: 10
<212> TYPE: PRT
<213> ORGANISM: Fossa fossana

<400> SEQUENCE: 36

Pro Pro Pro His Pro His Ala Arg Ile Lys
1 5 10

<210> SEQ ID NO 37
<211> LENGTH: 10
<212> TYPE: PRT
<213> ORGANISM: Viverricula indica

<400> SEQUENCE: 37

Pro Pro Pro His Pro His Ala Arg Ile Lys
1 5 10

<210> SEQ ID NO 38
<211> LENGTH: 10
<212> TYPE: PRT
<213> ORGANISM: Diceros bicornis

<400> SEQUENCE: 38

Pro Pro Pro His Pro His Ala Arg Ile Lys
1 5 10

<210> SEQ ID NO 39
<211> LENGTH: 10
<212> TYPE: PRT
<213> ORGANISM: Equus caballus

<400> SEQUENCE: 39

Pro Pro Pro His Pro His Ala Arg Ile Lys
1 5 10

<210> SEQ ID NO 40
<211> LENGTH: 10
<212> TYPE: PRT
<213> ORGANISM: Lama guanicoe pacos

<400> SEQUENCE: 40

Pro Pro Pro His Pro His Ala Arg Ile Lys
1 5 10

<210> SEQ ID NO 41
<211> LENGTH: 10
<212> TYPE: PRT
<213> ORGANISM: Physeter catodon

<400> SEQUENCE: 41

Pro Pro Pro His Pro His Ala Arg Ile Lys
1 5 10

<210> SEQ ID NO 42
<211> LENGTH: 10
<212> TYPE: PRT

<213> ORGANISM: Trichechus manatus

<400> SEQUENCE: 42

Pro Pro Pro His Pro His Ala Arg Ile Lys
1 5 10

<210> SEQ ID NO 43
<211> LENGTH: 10
<212> TYPE: PRT
<213> ORGANISM: Elephas maximus

<400> SEQUENCE: 43

Pro Pro Pro His Pro His Ala Arg Ile Lys
1 5 10

<210> SEQ ID NO 44
<211> LENGTH: 10
<212> TYPE: PRT
<213> ORGANISM: Oryctolagus cuniculus

<400> SEQUENCE: 44

Pro Pro Pro His Pro His Ala Arg Ile Lys
1 5 10

<210> SEQ ID NO 45
<211> LENGTH: 10
<212> TYPE: PRT
<213> ORGANISM: Lepus crawshayi

<400> SEQUENCE: 45

Pro Pro Pro His Pro His Ala Arg Ile Lys
1 5 10

<210> SEQ ID NO 46
<211> LENGTH: 10
<212> TYPE: PRT
<213> ORGANISM: Tarsius bancanus

<400> SEQUENCE: 46

Pro Pro Pro His Pro His Ala Arg Ile Lys
1 5 10

<210> SEQ ID NO 47
<211> LENGTH: 10
<212> TYPE: PRT
<213> ORGANISM: Cynopterus sphinx

<400> SEQUENCE: 47

Pro Pro Pro His Pro His Ala Arg Ile Lys
1 5 10

<210> SEQ ID NO 48
<211> LENGTH: 10
<212> TYPE: PRT
<213> ORGANISM: Tupaia tana

<400> SEQUENCE: 48

Pro Pro Pro His Pro His Ala Arg Ile Lys
1 5 10

<210> SEQ ID NO 49
<211> LENGTH: 10
<212> TYPE: PRT
<213> ORGANISM: Saimiri boliviensis

<400> SEQUENCE: 49

Pro Pro Pro His Pro His Ala Arg Ile Lys
1 5 10

<210> SEQ ID NO 50
<211> LENGTH: 6
<212> TYPE: PRT
<213> ORGANISM: Canis familiaris

<400> SEQUENCE: 50

Pro Pro Pro His Pro His
1 5

<210> SEQ ID NO 51
<211> LENGTH: 9
<212> TYPE: PRT
<213> ORGANISM: Eulemur fulvus collaris

<400> SEQUENCE: 51

Pro Pro His Pro His Ala Arg Ile Lys
1 5

<210> SEQ ID NO 52
<211> LENGTH: 9
<212> TYPE: PRT
<213> ORGANISM: Lemur catta

<400> SEQUENCE: 52

Pro Pro His Pro His Ala Arg Ile Lys
1 5

<210> SEQ ID NO 53
<211> LENGTH: 9
<212> TYPE: PRT
<213> ORGANISM: Eulemur fulvus fulvus

<400> SEQUENCE: 53

Pro Pro His Pro His Ala Arg Ile Lys
1 5

<210> SEQ ID NO 54
<211> LENGTH: 9
<212> TYPE: PRT
<213> ORGANISM: Hapalemur simus

<400> SEQUENCE: 54

Pro Pro His Pro His Ala Arg Ile Lys
1 5

<210> SEQ ID NO 55
<211> LENGTH: 9
<212> TYPE: PRT
<213> ORGANISM: Lepilemur edwardsi

<400> SEQUENCE: 55

Pro Pro His Pro His Ala Arg Ile Lys
1 5

<210> SEQ ID NO 56
<211> LENGTH: 9
<212> TYPE: PRT
<213> ORGANISM: Cheirogaleus medius

<400> SEQUENCE: 56

Pro Pro His Pro His Ala Arg Ile Lys
1               5

<210> SEQ ID NO 57
<211> LENGTH: 9
<212> TYPE: PRT
<213> ORGANISM: Daubentonia madagascariensis

<400> SEQUENCE: 57

Pro Pro His Pro His Ala Arg Ile Lys
1               5

<210> SEQ ID NO 58
<211> LENGTH: 9
<212> TYPE: PRT
<213> ORGANISM: Propithecus deckenii coronatus

<400> SEQUENCE: 58

Pro Pro His Pro His Ala Arg Ile Lys
1               5

<210> SEQ ID NO 59
<211> LENGTH: 9
<212> TYPE: PRT
<213> ORGANISM: Nycticebus coucang

<400> SEQUENCE: 59

Pro Pro His Pro His Ala Arg Ile Lys
1               5

<210> SEQ ID NO 60
<211> LENGTH: 10
<212> TYPE: PRT
<213> ORGANISM: Cavia porcellus

<400> SEQUENCE: 60

Pro Pro Pro His Pro Asn Ala Arg Ile Lys
1               5                   10

<210> SEQ ID NO 61
<211> LENGTH: 11
<212> TYPE: PRT
<213> ORGANISM: Rattus norvegicus

<400> SEQUENCE: 61

Pro Pro Pro Thr His Pro His Ala Arg Ile Lys
1               5                   10

<210> SEQ ID NO 62
<211> LENGTH: 11
<212> TYPE: PRT
<213> ORGANISM: Mus musculus

<400> SEQUENCE: 62

Pro Pro Pro Thr His Pro His Ala Arg Ile Lys
1               5                   10

<210> SEQ ID NO 63
<211> LENGTH: 9
<212> TYPE: PRT
<213> ORGANISM: Crocuta crocuta

<400> SEQUENCE: 63

Pro Pro His Pro His Ala Arg Ile Lys
1               5

<210> SEQ ID NO 64
<211> LENGTH: 11
<212> TYPE: PRT
<213> ORGANISM: Eliurus sp

<400> SEQUENCE: 64

Pro Pro Pro Thr His Pro His Ala Arg Ile Lys
1 5 10

<210> SEQ ID NO 65
<211> LENGTH: 11
<212> TYPE: PRT
<213> ORGANISM: Steatomys sp

<400> SEQUENCE: 65

Pro Pro Pro Thr His Pro His Ala Arg Ile Lys
1 5 10

<210> SEQ ID NO 66
<211> LENGTH: 11
<212> TYPE: PRT
<213> ORGANISM: Otomys angoniensis

<400> SEQUENCE: 66

Pro Pro Pro Thr His Pro His Ala Arg Ile Lys
1 5 10

<210> SEQ ID NO 67
<211> LENGTH: 11
<212> TYPE: PRT
<213> ORGANISM: Silky anteater

<400> SEQUENCE: 67

Pro Pro His Pro His Pro His Ala Arg Ile Lys
1 5 10

<210> SEQ ID NO 68
<211> LENGTH: 11
<212> TYPE: PRT
<213> ORGANISM: Procavia capensis

<400> SEQUENCE: 68

Pro Pro Pro Leu His Pro His Ala Arg Ile Lys
1 5 10

<210> SEQ ID NO 69
<211> LENGTH: 11
<212> TYPE: PRT
<213> ORGANISM: Didelphis marsupialis virginiana

<400> SEQUENCE: 69

Pro Pro Pro Thr His Pro His Ala Arg Ile Lys
1 5 10

<210> SEQ ID NO 70
<211> LENGTH: 11
<212> TYPE: PRT
<213> ORGANISM: Galeopterus variegatus

<400> SEQUENCE: 70

Pro Pro Pro His His Pro His Ala Arg Ile Lys
1 5 10